(12) United States Patent
Zabara

(10) Patent No.: US 8,684,901 B1
(45) Date of Patent: Apr. 1, 2014

(54) ELECTROMAGNETIC RADIATION TREATMENT FOR CANCER AND PATHOLOGICAL GENETIC REGULATIONS

(76) Inventor: Jacob Zabara, Miami Beach, FL (US)

( * ) Notice: Subject to any disclaimer, the term of this patent is extended or adjusted under 35 U.S.C. 154(b) by 622 days.

(21) Appl. No.: 12/951,621

(22) Filed: Nov. 22, 2010

(51) Int. Cl.
*A61N 1/00* (2006.01)

(52) U.S. Cl.
USPC .................................. 600/14; 607/2

(58) Field of Classification Search
USPC .......... 600/9–15; 607/1–3, 66, 67, 72–74, 76, 607/100, 101, 103, 901
See application file for complete search history.

(56) References Cited

U.S. PATENT DOCUMENTS

| | | | |
|---|---|---|---|
| 7,228,053 B1 | 6/2007 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,684,840 B2 | 3/2010 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |

OTHER PUBLICATIONS

Kirson et al.; Cancer Research; Disruption of Cancer Cell Replication by Alternating Electric Fields; Cancer Res 2004;64:3288-3295. May 3, 2004.
Kirson et al., Alternating electric fields arrest cell proliferation in animal tumor models and human brain tumors; PNAS/vol. 104/No. 24/ pp. 10152-10157. Jun. 12, 2007.

*Primary Examiner* — Charles A Marmor, II
*Assistant Examiner* — Carrie R Dorna
(74) *Attorney, Agent, or Firm* — Malloy & Malloy, P.L.

(57) ABSTRACT

An electromagnetic radiation treatment regime includes identifying a target area of a patient that comprises at least some cancer cells, or other cells amenable to pathological genetic regulations. An electromagnetic radiation source, for example, a low frequency and/or radio frequency electromagnetic radiation source, is selected, along with treatment session parameters, such as, pulse frequency, pulse duration, electrical current, magnetic flux density, and/or treatment session exposure time. An amount of electromagnetic radiation is applied to the target area, and a response to the electromagnetic radiation by at least some of the cancer cells in the target area is measured. Based on an evaluation of the measured response, the treatment parameters may be modified for one or more subsequent electromagnetic radiation treatment session.

19 Claims, 6 Drawing Sheets

ELECTROMAGNETIC RADIATION TREATMENT FOR CANCER AND PATHOLOGICAL GENETIC REGULATIONS

BACKGROUND OF THE INVENTION

1. Field of the Invention

Low frequency electromagnetic radiation and radio frequency electromagnetic radiation are applied separately or in combination with one another to a target area of a patient, wherein the target area includes at least some cancer cells, or other cells amenable to pathological genetic regulations. The electromagnetic radiation alters the control system of at least some of the cells forcing them to return to a normal cellular control system, and/or the electromagnetic radiation serves to promote apoptosis or cell death in at least some of the cells, with little to no affect on the surrounding normal cell population.

2. Description of the Related Art

Cells contain mechanisms that regulate and control their various activities, among these are the control mechanisms that maintain proper growth rates of a cell, as well as the timing of cell death, when appropriate. Normal cells grow or replicate in response to an external signal, such as a growth factor that acts on an extracellular membrane bound protein, initiating a signaling cascade that ultimately leads to cell growth. For example, nerve growth factor, platelet derived growth factor, and epidermal growth factor, represent three such factors. Thus, growth in a normal cell is externally regulated and includes an important external input.

Normal cells also include mechanisms which control programmed cell death, or apoptosis. It is important that cells die off in order to limit the number of genetic mutations in a population of cells, which occur more frequently with increased cell divisions, as well as to keep tissues and organs functioning properly.

A number of factors contribute to the control and orchestration of cell growth, as well as cell death. Perhaps the most basic of these is deoxyribonucleic acid ("DNA"). DNA is a complex biomolecule comprised of a series of corresponding base pairs of nucleic acids. These base pairs may have positive or negative charges, which therefore render positive or negative charges at various points along the DNA molecule. Due in part to the charge distribution, DNA can assume a number of shapes or conformations depending on the quantity and movement of charge in the biomolecule. For instance, DNA can be in a linear conformation with a negative charge in its base pairs, thereby forming double helix as is the case with nuclear DNA. It can also be in a circular form, such as in mitochondrial or bacterial DNA. Thus, DNA comprises the building blocks from which cells are formed.

Moreover, DNA contains the genetic information of the cell, and must be copied or replicated each time the cell divides. Similarly, DNA strands must be separated and sorted into dividing cells during mitosis, i.e., growth, and meiosis, i.e., reproduction, in order to convey the genetic information to the next generation of cells. Therefore, these processes also affect the rate of cell growth, and the conformation of the DNA molecule affects the replication, mitosis, and meiosis processes.

Microtubules also affect cell growth. A microtubule is a hollow cylindrical polymer dipole with its negative pole at the centrosome of the nucleus of a cell and its positive pole at the cell membrane. Microtubule growth occurs at the positive pole at the cell membrane, and therefore can be said to radiate out from the centrosome. Accordingly, microtubules connect the cellular membrane to the nucleus of a cell. Microtubules are also used within the nucleus to guide separating DNA strands during mitosis.

Energy drives the many processes in a cell, including growth, DNA replication, mitosis, and meiosis. The cell is a self regulating system where the functions are regulated within the energy level required. More in particular, the cellular control system sets the level of energy required for a specific function of the cell. This energy, in the form of adenosine triphosphate, or ATP, is synthesized in the mitochondria of the cell.

A proton driven ATP synthesis is a critical mechanism of the cellular control system. Specifically, the electron transport chain is a series of proteins associated with the mitochondrial membrane that transfer electrons stepwise between the proteins. Simultaneously, protons are pumped against an electrochemical gradient to the exterior of the membrane. Energy is temporarily stored in this proton gradient. Upon flowing back through the inner membrane, these protons are acted upon by the membrane bound enzyme ATP synthase to relinquish this energy to ATP, an energy storage mechanism which stores this energy in phosphate bonds.

The protein cytochrome C is an important component of the electron transport chain located in the inner mitochondrial membrane. Rather than being membrane bound, cytochrome C is loosely associated with the inner membrane by covalent bonds and flows along the inner membrane. Furthermore, cytochrome C has a heme group containing iron that allows cytochrome C to transport electrons between proteins. It is a central component of the electron transport chain and ATP synthesis.

Significant energy is produced through ATP synthesis mediated by the electron transport chain. For instance, the protons pumped across the membrane exert an electrochemical gradient reaching about 60 to 100 milliVolts ("mV"). This is in addition to the normal potential across the membrane of about 140 mV. Accordingly, at its maximum, the total potential is in a range of about 200 to 240 mV. Moreover, with a low proton gradient, electron transport occurs at a maximum rate, while an increase of the proton gradient causes a decrease in electron transport. Thus the magnitude of the electrochemical gradient can affect both the rate and direction of the electron transport, in turn determining the amount of ATP generated.

Cellular energy production does not change gradually or continuously, but jumps between different levels, wherein different levels of energy are required to perform different cellular functions. For instance, the electron transport chain can operate to produce energy at a basic level, such as to maintain resting membrane potentials, etc., or jump to a new level as required for meiosis and cell division, etc., or jump to a functional level for secretion, contraction, etc. Once the energy is produced, it is stored in the phosphate bonds of ATP.

The discharge of energy from ATP can be accomplished by hydrolyzing the energy rich phosphate bonds. A first hydrolysis step reduces ATP to adenosine diphosphate, or ADP. A subsequent step reduces ADP to adenosine monophosphate, or AMP. A further step reduces AMP to pyrophosphate. Each of these steps hydrolyzes one phosphate bond, releasing significant energy to be utilized by the cell in various ways, such as to maintain membrane potential, enzymatic activity, protein synthesis, mitosis, etc. Corresponding with each hydrolysis step is a decrease of the electric charge of the molecule as ATP has a negative electric charge of four; ADP, three; AMP, two; pyrophosphate, one.

Proteins also affect the rate of cell growth and death. For instance, proteins are critical to a variety of cellular processes, including ATP synthesis, signal transduction, cell division, secretion, etc. Proteins are comprised of a series of amino acids and assume three dimensional conformational shapes. Moreover, proteins may have positive or negative charges appearing at various points in the molecule, often in relation to amino- or carboxyl-groups or charged side chains. For example, in the circular form of a molecule, there may be a negative charge at one pole and two positive charges at the other pole, the charges themselves, being attractive, contribute to a circular form of the molecule. For instance, the amino acids glutamine and arginine, at each pole, can assume this charge of positive and negative.

Complex proteins can assume any of at least three (3) energy states, namely, from lowest to highest: linear; circular; or twisted. A possible intermediate horseshoe form exists between linear and circular in energy. As a result of charge differential over the molecule, membrane proteins are dipoles which can turn and twist under electric field changes to the membrane potential. These molecules can be linear or circular, horseshoe or twisted in their conformation, each having a corresponding electrochemical state. Depolarization of the membrane can change the conformation of the protein to an active state, such as from a linear to a circular conformation. Associated with the twisted form of the protein is a distribution of negative and positive charges along the molecule which represents the highest energy state of the molecule, and thus, when the molecule changes conformation into the circular form, a significant amount of energy is released.

Conformational changes of membrane bound proteins can be affected by the membrane potential, as is evidenced in the example of the $Na^+/K^+$ voltage gated ion channel. Specifically, there is a net amount of potassium ion (K+) inside the cellular membrane and a net amount of sodium ion (Na+) outside, wherein the membrane is permeable to potassium ion (K+), but is impermeable to sodium ion (Na+). In nerve and muscle cells, when the membrane is depolarized upon the application of electric current, the voltage gated ion channel is activated, initiating an action potential across the membrane and inducing a conformational change in the voltage gated ion channel, which in turn allows sodium ion (Na+) to enter the cell. The subsequent flow of potassium ion (K+) across the membrane repolarizes the membrane, to a potential in the range of approximately 50 to 100 mV.

There are many types of membranes within a cell, each having a membrane potential. The membranes include the cellular outer membrane, the mitochondrial inner and outer membranes, and the nuclear membrane. The cellular membrane can be described as a lipid bilayer with a mosaic of protein impregnations or imprints. Here, the membrane potential is established by a negative charge on a protein whose hydrophilic end projects into the interior of the cell. This potential determines the movement of ions and molecules across the membrane, such as discussed above for potassium ions ($K^+$) and sodium ions ($Na^+$). However, it is also possible that protons ($H^+$) also move across the membrane, as a consequence of electron transport as described above in relation to ATP synthesis at the mitochondrial membrane. The membrane of the mitochondria involves the control of metabolism, mainly oxidative, by its potential, and ATP synthesis via electron-proton transport. The nuclear membrane, in the interior of the cell, contains the DNA of the cell within its boundary.

The lipid bilayer of a cellular membrane is interspersed with proteins of various composition and function which are charged, such that they have a dipole moment. Although all cells have a membrane potential or dipole moment, studies on membrane potential have been essentially limited to muscle or nerve cells where changes in the membrane potential are the result of an electrical signal. In muscle cells, this electrical signal initiates contraction of the muscle. In nerve cells, this electrical signal initiates the transmission of neurotransmitters between neurons.

Although all cells exhibit electrical properties, this has been investigated seriously only in nerve, brain and muscle cells, and the action potential is the predominant observation. All cells have a membrane potential, but only nerve and muscle cells are able to produce an action potential which is both a signaling and activating mechanism. The action potential normally is initiated at one end of a nerve or muscle cell by a depolarization of the membrane, resulting in a reduction of the magnitude of the potential. At a certain point of depolarization, called threshold, the action potential is discharged and is self propagated to the other end of the cell to end in a synapse or junction, where it generates a depolarization called a synaptic potential. The depolarization causes the release of a neurotransmitter which diffuses across the synaptic gap to depolarize the postsynaptic cell body (which contains the nucleus, mitochondria, ribosomes, etc.), to produce an action potential in the postsynaptic cell which can repeat this process.

The nerve cell, or neuron, may be either excitatory or inhibitory. The excitatory neuron acts as previously described to produce a depolarization. On the other hand, the inhibitory neuron releases an inhibitory neurotransmitter which acts to hyperpolarize the postsynaptic cell body, creating an increase in the magnitude of the membrane potential and can prevent activity or an action potential in the postsynaptic cell.

Changes in the cellular membrane potential of a postsynaptic cell can cause a change in the genetic material within the nucleus of that cell. For example, the action potential impacting the cell body of a neuron, or nerve cell, produces a depolarization which activates the FOS gene which is related to growth and regulation. FOS is also a known proto-oncogene, meaning that an appropriate virus can transform it into an oncogene, thereby initiating a cancerous process.

There are relevant functions which membrane polarization regulates. For instance, in the neuronal membrane, polarization results in the switching on of the action potential, also referred to as depolarization of the membrane to threshold. The membrane acts as a semiconductor where current can be turned on or off, wherein the transport system or other function can be turned off by hyperpolarization of the membrane.

Although the membrane potential is a Donnan or electrochemical equilibrium potential, it requires an appreciable amount of energy to maintain it. To maintain the membrane potentials, mitochondrial energy production is needed to synthesize ATP, which is used as the energy source separating ions across the membrane and maintaining the membrane potential. For example, the inner membrane of the mitochondria maintains a membrane potential of about 140 mV as a result of the Na+/K+ voltage gated ion channel. However, the membrane potential can increase anywhere from about 60 to 150 mV due to the accumulation of protons on the cytoplasmic side of the membrane, for a total potential in the range of about 200 to 290 mV. Accordingly, a significant amount of energy is required by the cell to maintain membrane potentials, as well as cellular processes within the cell that keep the cell functioning normally.

Unlike normal cells, abnormal cells do not possess the normal cellular control mechanisms and instead exhibit, among other things, uncontrolled cell growth and immortality. For instance, abnormal cells may have genetic mutations, such as gene deletions, additions, point mutations, etc., that result in the interference of normal cell functioning and processes. This is the case in cancer cells, as well as cells infected with a virus such as H1N1 influenza, more commonly referred to as swine flu, or human immunodeficiency virus ("HIV"). Moreover, cancer cells and virally infected cells share some of the same fundamental components and mechanisms.

One of the features common to abnormal cells such as cancer cells and virally infected cells is an uncontrolled growth rate. For instance, the cancer cell appears to have an almost constant signal to grow and reproduce. Specifically, growth or reproduction of the cancer cell is a result of a signal to grow and reproduce that is internally generated by the cancer cell. In other words, the cancer cell can grow in the absence of outside or external signals. This is in stark contrast to normal cells which grow and divide only in response to an external signal such as a growth factor. Accordingly, growth of cancer cells is entirely internally regulated and independent of the limitations of its environment, and therefore can grow continuously. Indeed, this uncontrolled growth is a major factor contributing to the production of tumors in cancer tissue.

A cancer cell's development can be broken into two phases, wherein the cancer cell behaves differently in each phase. The first phase is called initiation or promotion, and occurs when the cancer cell is first initiating and developing. This phase is generally accepted to be reversible. The remaining phase of the cancer cell's development is called progression and is considered to be irreversible. During this phase, the cancer cell propagates and proliferates, and can lead to the growth of tumors, invasion of neighboring tissues, and even metastasis to distant parts of the body. In order for the cancer cell to metastasize, it must break away from its adhesion to adjacent cells or the extracellular matrix and enter the blood or lymph stream. Then the cancer cell eventually adheres to another tissue, organ, or cellular structure.

In a number of aspects, including growth, an infected cell acts similarly to a cancer cell, except that the progeny are viruses rather than cells. Once inside a host cell, viral DNA is integrated into the host cell DNA through a process called transgenesis. Depending on the point of insertion, transgenesis may inactivate a tumor suppressor gene which repairs damage, and therefore, renders the cell incapable of repairing damage. This can lead to increased incidence of genetic mutations and, ultimately, cancer in the cell. A similar result may occur from infection by an oncogenic virus, which induces cancerous type growth in the cell. Regardless of the method of transgenesis, once integration of viral DNA into the host genome is complete, the virus induces the host cell to continuously replicate, thereby also replicating the viral DNA. This replication occurs until the cell bursts, releasing a multitude of virus molecules into the body. Indeed, this is the goal of the virus, allowing its genes to propagate throughout a host organism. Importantly, the signal to replicate comes from the virus itself, and therefore, similar to a cancer cell, it is internally controlled. Since it does not rely on external factors for growth, the virally infected cell can continue to grow continuously until the cell bursts. Thus, the cancer or infected cell supersedes the control system of the normal cell regarding growth.

Apoptosis, or programmed cell death, is also a part of a normal cell's control system. Abnormal cells, such as the cancer cell and virally infected cell, no longer have a signal to initiate apoptosis and, therefore, these cells do not die off, rather, they become immortal.

Cellular structures and molecules are known to exhibit electrical and magnetic properties. For example, as previously discussed, molecules such as proteins and DNA can have charged regions or components, whether positive or negative, which contribute to the electrical activity of the molecule. Membranes also have electrical properties as a result of the electrochemical potential established and maintained by the presence and movement of ions around and across the membrane. As mentioned previously, most of the information concerning electrodynamics of the normal cell has been obtained from studies of nerve and muscle cells.

Cellular structures and molecules also exhibit magnetic properties. For instance, the protons within nuclei of cells are responsive to a magnetic field. Since each proton is a dipole, it will align or spin in a particular direction, either up or down, when placed in a magnetic field. Placing a cellular sample in a steady state magnetic field results in the orientation of the protons of the cellular sample so they spin in the same direction, i.e., all up or all down. Application of a magnetic pulse, 90° out of phase, excites the protons of the nuclei and forces the protons into the transverse plane. Subsequent to the application of the magnetic pulse, the protons return to their original position generated by the steady magnetic field, known as relaxation. This relaxation has a characteristic time constant, or duration of excitation, unique to each cellular sample type. For instance, the time constant is different for different types of tissues of the body, and the time constant for cancer tissue is different than for non-cancerous tissue of the same type. Fluids have a relatively long time constant, in the range of about 1,500 to 2,000 milliseconds ("ms"), whereas water containing tissues have a time constant of about 400 to 1,200 ms, and fatty tissues have a shorter time constant in the range of about 100 to 500 ms.

Thus, protons in different tissues of the body have different periods of excitation duration, or time constants. An example of this is presented in Table 1 below showing the excitation times of proton populations for each of two different magnetic flux densities, 0.5 Tesla ("T") and 1.5 T:

TABLE 1

| Proton Population | 0.5 T | 1.5 T |
|---|---|---|
| Spleen | 760 ms | 1,025 ms |
| Liver | 395 ms | 570 ms |
| Fat | 192 ms | 200 ms |
| Muscle | 560 ms | 1,075 ms |
| CSF | — | 2,060 ms |
| Grey Matter (Brain) | 780 ms | 1,100 ms |
| White Matter (Brain) | 520 ms | 560 ms |

Moreover, the Larmor frequency ($r/2_\pi B$), which relates to the angular momentum of a spinning or precessing proton, for excitation of a proton ($H^+$) increases with an increase of the magnetic field, or magnetic flux density. For example, at 0.15 T it may be 6.39 MHz; at 0.5 T, 21.29 MHz; at 1.5 T, 63.87 MHz; at 3.0 T, 127.74 MHz.

To date, the utilization of the electrical and magnetic properties of cellular components and molecules to affect changes in a cell have been essentially limited to cardiac pacemakers or defibrillators, the magnetic stimulators, and the magnetic resonance imaging (MRI).

The cardiac pacemaker is used therapeutically to deliver an electrical current or voltage directly to the heart muscle cells, usually those in the ventricle, in order to correct fibrillation or tachycardia. Specifically, the rate at which the heart pumps blood is controlled by the medulla in the brain which sends signals via sympathetic and parasympathetic nerves to the SA node of the heart to modulate the nodes' oscillatory depolarizations, thus producing the heart rate. If the heart rate becomes too high, as in the case of tachycardia, fibrillation may result, which is characterized by groups of ventricular muscles contracting independently of the SA node and each other, or asynchronously, resulting in a negligible blood pressure. The defibrillator corrects this by temporarily stopping the heart with an intense electric shock, after which, the heart should return to its normal rhythm. The pacemaker therefore utilizes the electrical properties of cells and neuronal signaling to effect a change in the body.

The magnetic stimulator, such as manufactured by MagStim and Danntec, has been used for diagnostic purposes, rehabilitation and psychological research. Essentially, the magnetic stimulator delivers current or voltage to nerve cells, either in the brain or peripherally, via a magnetic field to depolarize motor cortex neurons and measure nerve conduction time. This involves the use of magnetic coils placed over a target area to produce a pulsed magnetic field, thereby inducing an electric field and resulting in an electrical current applied to a targeted area of the brain. Despite the use of a magnetic field to generate an electrical current, the magnetic field is not directly utilized for therapeutic purposes.

Magnetic resonance imaging ("MRI") utilizes an EMR field applied to selected regions of the body for the purpose of producing an image. To accomplish this, magnetic fields are applied to specific regions of the body in order to excite particular cellular components, such as protons within molecules or nuclei of cells. The excited protons or nuclei then release this excess energy and return to equilibrium levels via the process of relaxation, and the time required for this return to equilibrium is known as the relaxation time. Raymond Damadian discovered in the early 1970's that the relaxation time of cancer cells is different from the neighboring normal cells, and thus the presence of cancer can be determined and its magnitude observed. Accordingly, MRI utilizes the EMR properties of cells to provide an image of the tissue or organ, however, it does so based upon the magnetic properties of cells, without utilization of the electrical currents induced by the MRI equipment itself.

Despite the fact that medical technology has utilized both electrical and magnetic properties of cells, cellular components and molecules independent of one another, no known medical technology simultaneously controls and utilizes both electrical and magnetic properties for therapeutic treatment purposes.

The interrelation between electric and magnetic properties of cells may be observed. For example, when tissues or organs or body parts are exposed to a changing magnetic field, an electric field is produced which causes a current based on ionic movement. Positive and negative ions move in opposite directions, similar to the interior of an electric battery. Accordingly, there is energy imparted by the magnetic field. For example, according to quantum mechanics, there are only two possible states of a proton ($H^+$), with values of $\pm \frac{1}{2}$, corresponding to whether the proton is in the spin up or spin down direction. The energy (E) of each state is:

$$E = \mu B = rhI \cdot B$$

where B is the magnetic field, h is Planck's constant, $\mu$ is the angular momentum, r is the gyromagnetic ratio, and I is the angular momentum quantum value ($\frac{1}{2}$ for protons).

Present treatment regimens for cancer patients include surgery, chemoradiation, and pharmaceutical drugs, which are directed primarily to the removal or eradication of the cancer cell population. However, these methods can not be limited solely to the cancer cell population, and as a result, normal healthy cells are also removed and/or eradicated in the process.

For example, surgery has been a common technique for combating cancer, and is often used for the removal or excision of tumors. However, there are significant risks involved with surgical treatment, as with any surgery, including possible complications, hemorrhaging, adverse reactions to aesthesia, etc. Moreover, surgical removal of cancer cells is only feasible once the cancer has grown to a substantial population, and can therefore not be implemented for precancerous or early stages. While precancerous cells exhibiting abnormal characteristics can be surgically removed in order to avoid the development of cancer, this often involves removal of surrounding normal healthy tissue as well. Further, surgery may not be practical for the treatment of other forms of abnormal cells, such as those infected with a virus.

Chemoradiation has also been used to treat cancer. The main problem with this therapy is safety. Chemoradiation involves subjecting tissue to toxic levels of radiation, which is intended to damage the DNA of the cells within the irradiated tissue, and thereby prompt cell death. However, this is a highly risky procedure as it is difficult to isolate just the cancer cells, and so the surrounding healthy tissue cells are also irradiated, damaged, and die. Because of its safety problems and lack of specificity, chemoradiation can only be utilized a limited number of times. Moreover, the cancer cell can mutate to become resistant to chemoradiation, further complicating treatment. Similar problems would be encountered if chemotherapy or chemoradiation were used to treat other abnormal cells, such as virally infected cells.

Cancer research, and in particular, research guided by the National Institute of Health, has been aggressively pursuing pharmaceutical treatment regimens since the discovery of the first significant anticancer drug, cis-platinum over fifty years ago. However, the results have not been particularly significant given the effort and funding levels directed to this research. For example, although a number of new anticancer drugs have been developed by pharmaceutical companies, they have not succeeded in significantly increasing present levels of effectiveness which, with few exceptions, have improved only minimally over the past fifty years. Also, most if not all pharmaceuticals for treating cancer produce significant adverse side effects. This is also the case for many of the antiviral drugs on the market. Thus, it appears critical to develop a new treatment regimen that could complement, if not replace altogether, present treatment regimens. It would be significantly beneficial for such a new treatment regimen to comprise none of the harsh and often detrimental side effects of known treatment regimens.

It is evident that known treatment regimens for cancer cells are non-specific, and equally and adversely impact all cells, normal and abnormal, in an affected area. More in particular, the known treatment regimens involving chemoradiation and/or pharmaceuticals are highly toxic to all cells and produce significant adverse side effects, and known treatment regimens requiring surgery involve removal of healthy cells along with target cancer cells. In any case, the known treatment regimens for cancer cells are simply not completely effective. Accordingly, the medical community needs a safe and effective treatment regimen for cancer cells.

SUMMARY OF THE INVENTION

The present disclosure is directed to a method for treatment of cancer cells and pathological genetic regulations of other cells with electromagnetic radiation. The present method includes identifying a target area comprising a plurality of target area cells, wherein at least some of the target area cells comprise cancer cells. In at least one embodiment, the method also includes isolating the target area, however, it is envisioned that in at least some applications, the target area will include the entire body of the patient, in which case, isolation is not required.

The present method also includes selecting a source of electromagnetic radiation, for example, low frequency electromagnetic radiation and/or radio frequency elector magnetic radiation. Further, the method includes selecting treatment parameters for an electromagnetic radiation treatment session. The treatment parameters include, but are not limited to, a pulse frequency of the electromagnetic radiation, the pulse duration of the electromagnetic radiation, an electrical current, a magnetic filed density, and a treatment session exposure time.

The electromagnetic radiation treatment regimen also includes initiating the electromagnetic radiation treatment session, and applying an amount of electromagnetic radiation from the selected electromagnetic radiation source(s) to the target area in accordance with the treatment parameters selected.

Additionally, the present method further comprises terminating the electromagnetic radiation treatment session. After the session is terminated, the present method provides for measuring a response of at least some of the plurality of target area cells to the electromagnetic radiation treatment session, and evaluating the response of the plurality of target area cells measured to the electromagnetic radiation treatment session. Based upon the response of the target area cells measured, revised treatment parameters may be selected, and one or more subsequent treatment session may be conducted.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
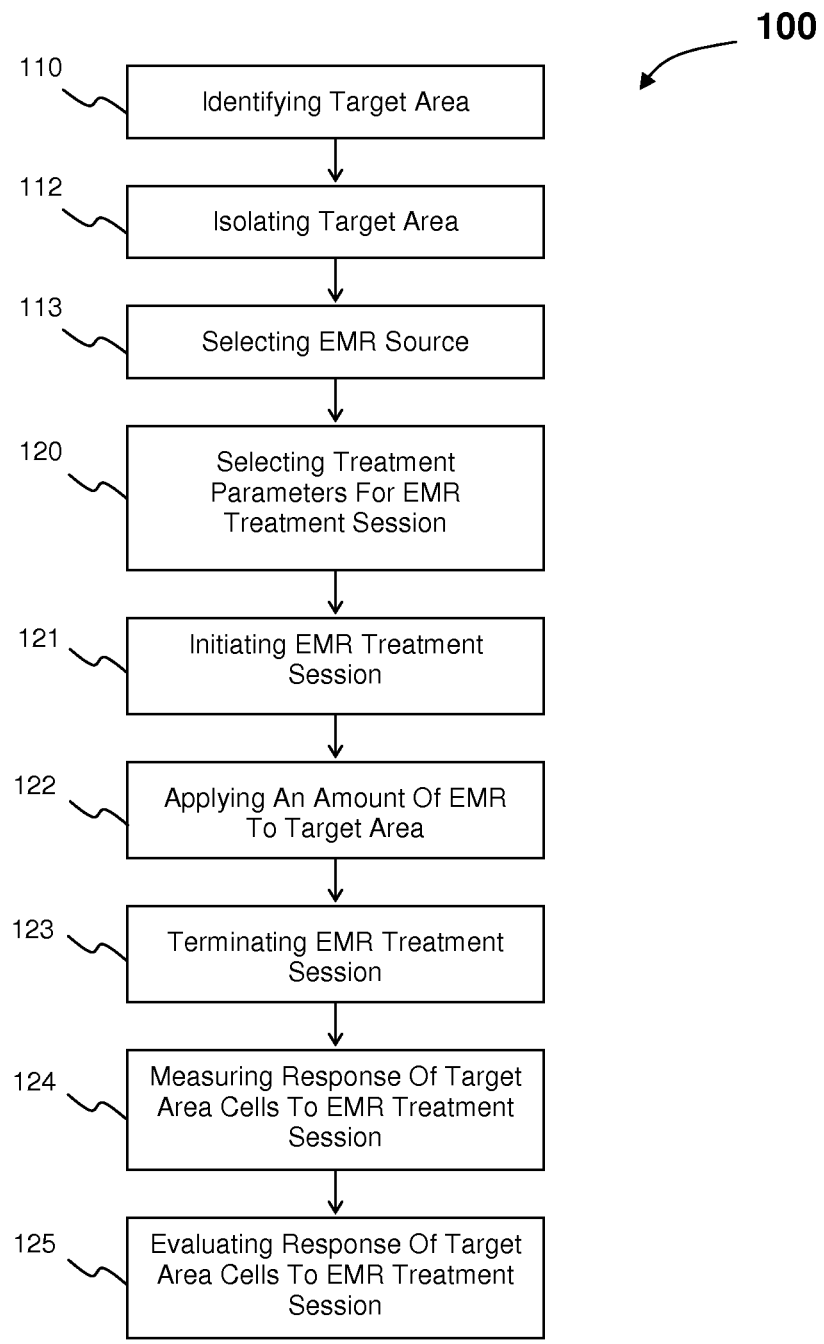
FIG. 1 is a schematic representation illustrative of one embodiment of an electromagnetic radiation treatment regimen in accordance with the present disclosure.

The treatment regimen of the present disclosure utilizes electromagnetic radiation ("EMR") to treat cancer cells, or other cells amenable to pathological genetic regulations. The method of the present disclosure represents an ensemble of subcellular elements targeted substantially simultaneously to interfere with a cancer cell's control system, and to restore a normal control system to the cancer cell. More in particular, the present method utilizes both electrical current and magnetic fields as significant vehicles of action on specific molecular and atomic components of a cancer cell, such as, the protons and electrons of the cancer cell, to elicit a beneficial therapeutic effect. The present method takes advantage of the significant differences in the electromagnetic properties of normal and cancer cells. Specifically, the differences between the electromagnetic properties of normal cells and cancer cells transcend the molecular realm, and extend into the quantum mechanism realm. While the present EMR treatment methodology is disclosed hereinafter with a primary focus on the treatment of cancer cells, it is understood to be within the scope and intent of the present disclosure to apply the present EMR treatment regimen to other abnormal cells including, but not limited to, cells affected by infectious diseases such as HIV/AIDS, H1N1, etc., which are amenable to pathological genetic regulations The method of the present disclosure provides a significantly greater safety profile than the previously known methods of treating cancer cells, such as, surgery, chemoradiation, and/or pharmaceutical treatment regimens. The safety of the present method inures from the electrodynamic differences between the cancer cell and the normal cell, for example, the metabolic rate of the cancer cell is much greater than a normal cell, which plays a role in the safety profile of the present method.

Further, the present treatment regimen can be used to treat abnormal cells associated with the at least the following types of cancer: 1) oral cavity and pharynx; 2) esophagus; 3) stomach; 4) small intestine; 5) colon or rectum; 6) liver; 7) pancreas; 8) larynx; 9) lung; 10) skin melanoma; 11) breast; 12) uterine cervix; 13) ovary; 14) prostate; 15) bladder; 16) non Hodgkin's lymphoma; 17) Hodgkin's disease; 18) multiple myeloma; 19) leukemia; 20) brain and nervous system; 21) thyroid; 22) eye; 23) kidney and renal pelvis; 24) testis; 25) uterus, corpus; 26) soft tissue; 27) bone; and 28) gallbladder and biliary. As noted above, the present EMR treatment methodology may also be utilized fro the treatment of other abnormal cells including, by way of example only, cells affected by viral infections resulting from influenza A ("H1N1"), also known as swine flu, human immunodeficiency virus ("HIV"), and acquired immunodeficiency virus ("AIDS"). Implementation of the treatment regimen of the present disclosure results in an interference with the control system of cancer cells, halts the progression of the cancer, and can even prevent the initiation of the infection or cancer.

Cellular Control Systems

The control system of a cell is designated as one of three types: 1) bioproportional control, 2) bioderivative control and 3) biointergral control, each indicative of the operation of the control system in physical and electrical analysis. Bioproportional control is present in a cancer cells throughout its reproductive activity, and allows for significant changes in a normal cell as it transforms into a cancer cell. This is not a statistical series of events based on randomness, but, rather, directed events occurring in a specific sequence which determine the survival and development of a cancer cell. Bioderivative control regulates cell division and its underlying DNA processes. In cancer cells, bioderivative control is present and regulates the initiation, or beginning phase, but not the progression, or final phase. Biointergral control addresses small errors which occur repeatedly over time.

Implementation of the present electromagnetic radiation ("EMR") treatment regimen introduces deliberate errors into the control system(s) of a cancer cell, to counteract the cell's reproductive and survival functions, as discussed in greater detail hereinafter.

Low Frequency ("LF") Electromagnetic Radiation Treatment

Low frequency ("LF") electromagnetic radiation is utilized in the present EMR treatment regimen to produce a pulsed magnetic field of low frequency in a range of about 0.5 to 200 Hertz ("Hz") resulting in a pulsed electric field. The pulsed electric field results in an alternating current acting upon the critical membranes of the cell, most directly on the cellular membrane. The LF electromagnetic radiation is achieved through the use of LF coils, which are usually circular or double constructed and are designed for to apply LF electromagnetic radiation to preselected regions of the body in a similar manner as the RF coils discussed hereinafter. The main effect of the application of LF electromagnetic radiation is to change the polarization of the membranes of target cancer cells.

The membrane polarization change is a function of the intensity, frequency, and direction of the alternating current generated by the magnetic field described by the following hyperbolic relationship:

$$dB/dt = C \cdot R[1+D/TC]$$

where dB/dt is the rate of change of the magnetic field (B), D is the time for a magnetic pulse to reach maximum and TC is the cancerous tissue's electrical time constant, which is a function of the dielectric, resistive, and magnetic properties of the cancerous tissue. C is a constant for the tissue radius and the magnetic field orientation.

Activation of protons by an appropriate magnetic field can increase the membrane potential and augment ATP synthesis, producing increased energy for the cell. Conversely, deactivation of protons by an appropriately oriented magnetic field can decrease or prevent ATP synthesis, and thus significantly diminish the energy available to a cancer cell.

The specific pathway(s) of electrical current through cancerous tissue is difficult to predict, since the tissue segment contains blood vessels, connective tissue, etc. However, the present EMR treatment focuses the positive polarity of the electric field within the cancerous tissue and the opposite, negative polarity of the electric field outside the cancer cell to affect the membrane potential. For example, to decrease activity of the membrane, the electric field has a direction of positive polarity within the cancerous tissue and negative polarity outside the cancerous tissue, resulting in a hyperpolarization of the membrane. The frequency, intensity, and direction of the magnetic field will be selected and adjusted based upon the nature and type of target cancerous tissue.

Radio Frequency ("RF") Electromagnetic Radiation Treatment

In at least one embodiment, the EMR treatment regimen of in accordance with the present disclosure comprises applying radio frequency ("RF") electromagnetic radiation to target cancer cells, in order to produce a direct magnetic field effect on nuclei and electrons in the cancerous tissue. More in particular, RF electromagnetic radiation is utilized in the present EMR treatment regimen to affect ATP synthesis, cytochrome C, protons and electrons of the electron transport chain, and DNA structure.

A radio frequency electromagnetic radiation coil is utilized both to supply electromagnetic radiation to affect the nuclei and electrons of a target cell, as well as to detect nuclear or atomic magnetic signals generated in the cancerous tissue. A receiver is utilized to demodulate the significant signal from the carrier frequency. The radio frequency pulses are generated with center frequencies, bandwidths, amplitudes and phases being preselected based upon the type of cancerous tissue being treated, and its location with the patient's body. More in particular, the bandwidth is selected to correspond to the thickness of the cancerous tissue. The duration or shape of the radio frequency pulse relates to the bandwidth, while the amplitude of the radio frequency pulse determines the intensity of the magnetic field. In at least one embodiment, the radio frequency pulse envelope can be produced by digital means.

In at least one embodiment of the present EMR treatment regimen wherein RF electromagnetic radiation is applied, RF electromagnetic radiation coils are arranged parallel to an axis of the patient, i.e., the coils have the same axis as that of a portion of the patient's body being treated. The coils may be resistive, or superconducting, such as, helium cooled coils. Implementation of the EMR treatment regimen in accordance with the present disclosure may require utilization of one or more of a variety of RF electromagnetic radiation coils, including 1) head coil, 2) integral body coil, 3) spine coil, 4) neck coil, 5) abdominal coil, 6) chest coil, 7) knee coil, 8) shoulder coil, 9) flexible coils, 10) tempermandibular coil, etc. The RF electromagnetic coils may surround the entire body or only part of the body, or may be placed next to body or body part. Magnetic fields are developed by utilizing at least one coil, or several sets of coils, one for each spatial dimension, or functional initiative. The RF electromagnetic radiation coils may be used individually, collectively, or in groups. Moreover, directed windings are oriented in three orthogonal directions. RF electromagnetic radiation pulses or waves are applied repeatedly in a regulated pulse or wave sequence.

The therapeutic effect of the present EMR treatment is a function of the energy imparted by the magnetic field produced via the RF electromagnetic radiation. More specifically, the RF electromagnetic radiation excites the atoms or nuclei of the target cells. The duration of excitation of the atoms or nuclei can be determined by reorienting them under a steady magnetic field by a radio frequency pulse. For instance, in a steady magnetic field, a 90° radio frequency pulse excites the nuclei and pushes the oriented nuclei into the transverse, or perpendicular, plane. The nuclei then return to their original positions generated by the steady magnetic field, called relaxing, which has a characteristic time constant that defines the duration of excitation. The time constant is different for cancerous tissue than for other normal tissues of the body. It also varies for different tissues. Fluids have a relatively long time constant in a range of about 1500-2000 ms, water containing tissues have a time constant in a range of about 400-1200 ms, and fatty tissues have a relatively short time constant in a range of about 100-500 ms.

By implementing the present EMR treatment regimen, it is possible to selectively target protons ($H^+$) of protein, fat, carbohydrate, protein bound water, or bulk water. A frequency selective for RF electromagnetic radiation excitation is applied for each of the above entities, and can be applied for all of them at the same time or in sequence. For example, RF electromagnetic radiation can be used to activate fat or water by selection of the appropriate corresponding frequency. The frequency can be determined by the Larmor equation. For instance, water protons precess 220 Hz faster than fat protons when exposed to a magnetic flux density of about at 1.5 Tesla ("T"). Protons in protein bound water have a resonant frequency which is about 500 to 2500 Hz different from bulk water proton frequency. However, since protein bound protons and bulk water protons are in rapid exchange, the excitation can be quickly transferred from protein bound water to bulk water. Notably, these excitation times are increased in the case of cancer cells.

In at least one embodiment, the present EMR treatment regimen comprises enhancing or doping target tissues, such as cancers or tumors, with gadolinium, to increase the precessing frequency of protons. Other chemicals may also be utilized to enhance or dope target tissues. For example, xenon gas may be used to enhance spin effects by producing xenon in a hyperpolarized form, and causing an increased magnetization. The hyperpolarization can also be produced by rubidium vapour. For example, xenon is soluble in blood and has a high affinity for lipids. Rubidium vapour can be excited by a diode laser, and act on the electrons. After electronic polarization, the xenon nuclei are excited by contact with the rubidium atoms, and then cooled to xenon ice.

In one further embodiment, photons are utilized to augment the effect of electromagnetic radiation on electrons and protons. In one embodiment, a radioactive agent or pharmaceutical, such as technetium (Tc-99), which produces high energy photons, e.g., 140 kilo electron volt photons, is utilized. Technetium has a half life of about six hours and can be attached to a molecule which combines with a cancer cell. For instance, in one embodiment, Tc-99 methylene diphosphonate (MDP) can be injected intravenously and absorbed by, and bound to, bone as a result of osteoblastic activity caused by metastatic deposition.

Moreover, in at least one embodiment, application of RF electromagnetic radiation is repeated at suitable intervals to maintain the excitation for a considerable period of time. The Larmor frequency ($r/2_{\pi}B$) for excitation of protons ($H^+$) increases with an increase of the magnetic field. For example, at 0.15 T the Larmor frequency may be 6.39 megahertz ("mHz"); at 0.5 T, 21.29 mHz; at 1.5 T, 63.87 mHz; at 3.0 T, 127.74 mHz. Cancer cells have increased excitation times compared to normal cells. Thus the excitation duration of protons is appreciably greater when the proton is located in or within the immediate environment of an cancer cell. This indicates either an increased binding of the proton, or a decreased threshold, or a changed resonant frequency, in comparison to the normal cell. The cell's return to normal upon application of the present EMR treatment regimen can be observed by the cancer cell's excitation time becoming essentially the same as the excitation time of a normal cell.

Accordingly, the excitation time can also be utilized to measure the progress of the EMR treatment regimen. For instance, the electromagnetic radiation fields generated by the proton are detected via receiver coils. Thus, almost simultaneously with application of the EMR treatment regimen of the present disclosure, it is possible to measure the real time effect of the treatment.

Combined LF and RF Electromagnetic Radiation Treatment

In at least one embodiment of the present EMR treatment regimen, LF electromagnetic radiation is applied in conjunction with RF electromagnetic radiation as discussed above. Further, in one embodiment, the RF electromagnetic radiation and LF electromagnetic radiation are applied in series, whereas, in at least one further embodiment, the RF electromagnetic radiation and LF electromagnetic radiation are applied in parallel, or in other words, simultaneously. Appropriate shaped electromagnetic radiation pulses are generated at Larmor or other frequencies, and an alternating magnetic field of LF electromagnetic radiation is produced. With RF electromagnetic radiation, a steady magnetic field is employed.

A variety of known components may be arranged and utilized to produce the magnetic fields required for implementation of the present EMR treatment regimen to act on the cancerous tissue. For instance, a system can be used to generate and apply the required electromagnetic radiation. Such a system may include at least a configuration of directed windings, drivers, radio frequency electromagnetic radiation generators, low frequency electromagnetic radiation generators, power amplifiers, receiver windings, control electronics, frequency reference, receivers, demodulators, frequency oscillators, digital/analog converters, filters, mixers, preamplifiers, attenuators, an imaging component consisting of receiver windings and EMR coils, receivers, demodulators and acquisition picture, and a measuring component consisting of receiver windings and recorder.

A controller may be utilized to apply the appropriate frequency, duration, intensity, etc., and to drive the currents in windings or coils, which are directed three dimensionally upon the target tissue directly or in conjunction with a steady magnetic field. The electromagnetic radiation coils are arranged in different spatial planes with respect to the target tissue to focus the alternating or pulsed electromagnetic radiation field to the preselected target cells. These target cells may be located deep within tissue of the body, or may be located superficially on the body, such as on the skin. Furthermore, in at least one embodiment, the electromagnetic radiation coils are disposed or positioned perpendicular to a central axis of the target cells or tissues. In at least one other embodiment, the electromagnetic radiation coils are disposed or positioned parallel to the central axis of the target cells or tissue.

The effectiveness of the electromagnetic radiation coils can also be enhanced in a variety of ways. For example, a ferromagnetic material can be placed around at least one electromagnetic radiation coil to increase the effectiveness of the electromagnetic radiation field that coil generates. In another embodiment, at least one electromagnetic radiation coil is superconducting, thereby increasing the effectiveness of the field generated thereby. Moreover, the electromagnetic radiation field produced by an electromagnetic radiation coil can be focused and intensified by placing magnetic or paramagnetic material within or surrounding the target are of the body. In one embodiment, the magnetic or paramagnetic material is placed in or near the target area by injection of the material into nearby blood vessels. In another embodiment, the magnetic or paramagnetic material is placed externally to the target region, such as with an external magnetic device.

The frequency range of the electromagnetic radiation coils is either a radio frequency or low frequency. In the case of LF electromagnetic radiation coils, the electromagnetic radiation field produces polarizations of membranes in different target regions of the body of a patient depending on the size, orientation and geometry of the electromagnetic radiation coil with respect to the target area, the strength of the resultant alternating electromagnetic radiation field, and a frequency with respect to the target area of an alternating electromagnetic radiation field.

In the case of RF electromagnetic radiation coils, the electromagnetic radiation field produces activation or deactivation of the electron transport system or electrons or protons of nuclei in cancer cells in the target area depending on at least a size, orientation and geometry of the electromagnetic radiation coil, the intensity of the electromagnetic radiation field, and a frequency with respect to the target area of the steady state electromagnetic radiation field.

The controller further directs the frequency, duration and magnitude field in the radio frequency range. The Larmor frequency is the reference for the resonant frequency of the target nuclei. A magnetic field, specifically, a steady state magnetic field produced by a fixed magnet is utilized in conjunction with RF electromagnetic radiation. Further, X, Y, and Z directed windings are used, and refer to one spatial embodiment of the coils in orthogonal, or perpendicular, orientations. A receiver and a demodulator may be collectively employed to measure the excitation durations of nuclei in the cancerous tissue via receiver windings. Accordingly, and as noted above, the present EMR treatment regimen may be utilized both to affect treatment as well as to measure the effectiveness of the same.

Effectiveness of Electromagnetic Radiation Treatment

The EMR treatment regimen in accordance with the present disclosure comprises both an action and a signal. One of the effects of implementation of the present EMR treatment regimen is to initiate a memory so that effectiveness can increase over time. For memory to be initiated, EMR treatment is performed in a rapid sequence of signals which correspond to the sequential actions of the control system of the cell. Specifically, the sequential actions resulting from implementation of the present EMR treatment regimen in this manner begin with the cellular or plasma membrane, mitochondrial membrane, and nuclear membrane microtubules. Although, there are a number of other cellular components involved in the sequence, the affect of the present EMR treatment on the membranes of cancer cells is sufficient to establish the initiation of the cellular memory. The conformation of a specific membrane protein is a component of the memory, but overall memory corresponds to a dynamic control system in the living cell. To implement memory, the sequential actions within the control system should be those followed by EMR treatment.

It should be appreciated that implementation of the present EMR treatment regimen can assume a number of different forms, patterns or intensities depending on the nature of the cell, its location in the body, the stage of cancer or infection, the type of cancer or infection, etc. More in particular, the electromagnetic radiation field applied, as well as frequency, intensity, pulse, etc., are all preselected in accordance with the nature and location of the cancer cells within the patient's body. When the present EMR treatment regimen is implemented, the memory of the treated cancer cell will correspond to an integration of control system correction, and repeated treatments will demonstrate increasing effectiveness.

Animal Tissue Model

An animal tissue model may be utilized to demonstrate the electrical manifestations of a cancer cell, and its differences from the normal cell. This is important because, with the exception of nerve and muscle cells, there is virtually little that is known, studied, or investigated with regard to the electrical differences between normal and cancer cells.

Thus, the experimental model developed and disclosed herein is structured to measure electrical properties of the cancer cell, and compare these to the normal cell, as no such model is known to exist. This experimental model provides support for the science underlying the present EMR treatment regimen, and also assists in determining the parameters which would be most effective for the treatment. This model is developed for the investigation of cancer cells compared to normal cells, and is presented as an illustrative approximation of the results which may be obtained via implementation of the EMR treatment regimen in accordance with the present disclosure.

To begin, a cancer process is initiated in a cellular population of several thousand cells by utilization of a virus. The tissue can be excised from the host animal, such as a rat, and placed in a controlled environment. Electrodes are placed on or near the infected cellular population to measure electrical changes which emanate directly from the cellular membranes and membrane potentials. These signals are first amplified and then recorded. The first electrical signal observed will be a non-periodic oscillation which arises from the cancer process, and is not generated by normal cells. A single component of the oscillation lasts about 250 milliseconds and represents a large depolarization, essentially equal to the magnitude of the resting cellular membrane potential, followed by repolarization and hyperpolarization, wherein the hyperpolarization change lasts about 30 milliseconds.

The observation that this cellular and membrane activity is from isolated tissue indicates it is not initiated by way of its environment, such as hormones, nerves, etc., but rather is due to the cancerous process within the cell. This electrical activity is not present in the normal cell tissue, as noted above, even if the normal cell tissue is isolated, in the same way, i.e., isolated from the animal in vitro. Accordingly, the foregoing demonstrates that the control system of the cancer cell no longer relies upon an external component, and is independent of external influence.

In order to substantiate this observation, the cancerous tissue is left in contact with the animal and surrounding tissue, while recording during this same time period. No oscillations are observed. However, if the tissue is left in place, but simply isolated chemically or surgically, the oscillations appear after a lag time of approximately a minute. So that external input to these cells is definitely present and can prevent the oscillations during this period of time. What is meant by this period of time is that these are the first electrical changes that are observed by recording in this way. A minute lag time perhaps involves the lingering effects of the external input, or the time taken for the cancer cell's control system to achieve dominance.

This phase in the cancer cell's development is called promotion, and is generally accepted to be reversible. The present EMR treatment regimen can be implemented to substitute for external modulation of the cancer cell and replace it, to reverse and prevent development of the cancerous process to produce, in effect, a benign cancer which does not metastasize.

The remaining phase of the cancer cell's development is called progression and is considered to be irreversible. In the animal tissue model, this phase is correlated with an increase in frequency and magnitude of the oscillations from the cancer cells. More importantly, the hyperpolarization at the termination of the single oscillatory excursion is absent. In addition, the oscillations appear spontaneously at this time in the intact cancerous tissue. The hyperpolarization determines that there is a single oscillation. In the absence of the hyperpolarization, multiple oscillations, such as a train or complex, occur at a frequency which elevates the complex above baseline, and this pattern is repeated. This indicates that the energy necessary for this process is under the control of the mitochondria, and the hyperpolarization terminates that period of energy production resulting in a single oscillation. Implementation of the present EMR treatment regimen produces a hyperpolarizing current which would do the same and reverse the process to single oscillations, the promotion phase which is reversible.

To demonstrate these effects in the animal tissue model, acetylcholine is applied and combines with its receptor in the membrane, and decreases the membrane potential to initiate the cellular functions. In the nerve cell, this would include the action potential, as would also be the condition in the muscle cell. The effects of other pharmacological agents, which combine with protein receptors in the cellular membrane, can also be demonstrated. The effects include transforming the cancer cell, as observed by its membrane potential changes, from promotion to progression, and reversing the cancer cell's development from progression to promotion. Thus, not only promotion, but progression may be reversible upon implementation of the present EMR treatment regimen.

Affects of Electromagnetic Radiation Treatment

Implementation of the EMR treatment regimen as disclosed above produces at least the following two results: 1) restoration of the missing component(s) of the cell's normal control system, and/or impeding the activity of the cancer cell's control system; and, 2) initiating apoptosis in cancer cells. An essential element of the control system of any cell is energy generation, which occurs primarily in the mitochondria, and apoptosis, which is also primarily initiated in the mitochondria. To elicit the aforementioned results, the present EMR treatment regimen acts upon at least one of the following: 1) membranes, including cellular, mitochondrial, and nuclear membranes, and particularly focusing upon the membrane potentials or dipoles; and, 2) molecular or atomic entities, including protons, carbon and nitrogen nuclei, the heme group of cytochrome C, protein electron carriers (such as those of the electron transport chain), ATP synthase, DNA and microtubules.

The specific impact of implementation of the present EMR treatment regimen on the various cellular properties and cellular components is discussed in further detail in the following sections.

Membranes—Cellular, Nuclear, Mitochondrial

One result of the EMR treatment regimen of the present disclosure is to affect a cancer cell by producing a hyperpolarization therein, i.e., reducing the activity of the cancer cell. Since the cancer cell is hyperactive, or has a higher activity level than that of a normal cell, the present EMR treatment selectively targets and interferes with the increased activity of cancer cells, thereby minimizing, if not eliminating altogether, any negative impact on normal cells in proximity. Hyperpolarization at critical membranes of a cancer cell slows or prevents growth in the cancer cell, and may ultimately result in eventual cell death via apoptosis.

On the other hand, the present EMR treatment can also affect cancer cells by causing a decrease in a cancer cell's membrane potential, or depolarization, resulting in a decrease in the functional activity of the cell. A directional current in accordance with the present EMR treatment regimen can selectively depolarize or hyperpolarize the cellular membrane of the cancer cell. The directional current utilized by the present method has a frequency in the range of about 0.5 Hz to 1000 Hz, and in at least one embodiment, in a range of about 0.5 Hz to 200 Hz, depending on the type and location of the cell, for example, a cancer cell. The frequency of the directional current utilized in accordance with the present disclosure depends on the time constant of the membrane, as well as other factors.

In at least one embodiment, EMR treatment can also change the membrane potential by acting on the voltage gate, such as the $Na^+/K^+$ pump, by changing the conformation of the $Na^+/K^+$ pump between a linear form, having lower energy, and a circular or twisted form, having higher energy. The EMR treatment in accordance with the present disclosure can act directly on the cellular membrane of a cancer cell through a current effect which then continues to the mitochondrial inner membrane, nuclear membrane, and microtubule. Such a current effect is produced by low frequency ("LF") Electromagnetic radiation, as explained in greater detail hereinafter, and/or it may be produced by an adjunct implanted device, also described below.

The present EMR treatment acts on the mitochondria at several molecular and membrane sites, to produce a decrease in metabolism or apoptosis. The present EMR treatment is not structured to immediately destroy the cancer cell, as is the intent of surgery or chemoradiation, but rather to affect a more gradual and safer, transformation or elimination. EMR treatment in accordance with the present disclosure accomplishes the safe transformation or elimination of cancer cells by diminishing ATP production and decreasing the energy available to the cancer cell, without affecting the energy of the normal cells. In at least one embodiment, ATP production and energy in a cancer cell is reduced by changing the membrane potential of the inner mitochondrial membrane. In at least one other embodiment, ATP production and energy in the cancer cell is reduced by decreasing proton flow.

A change in the membrane potential of a cell can be transmitted from the cellular membrane to the mitochondrial and nuclear membranes. A change in membrane potential, and thus polarization of the membrane, results in a change in level of functional activity of the cell, and a change in energy generation, or set point. For example, an increase in the membrane potential of a cell decreases cellular function and decreases mitochondrial energy production. At the mitochondria, a change in the proton gradient across the inner mitochondrial membrane results in a change in the function of the electron transport chain proteins, and therefore, ATP production, as well as membrane potential, electron potential, NADPH synthesis, ATP, active transport, and heat production. The foregoing processes affect energy production which is required for the cancer cell to conduct other cellular processes, such as DNA activity. Accordingly, a change in the set point and energy production correspondingly produces a change in DNA activity. The present EMR treatment can thus interrupt DNA activity by hyperpolarizing at least the cellular membrane, and substantially, if not completely, inhibit DNA activity.

One effect of implementation of the present EMR treatment regimen is to decrease the rate of energy production in the cancer cell. More in particular, upon decreasing the energy production in cancer cells via the present EMR treatment, any excess energy present in the cell is released as heat and/or is stored as useful energy in ATP.

Spin Frequency

As noted above, the present EMR treatment reduces the energy available to the cancer cell, i.e., decreasing the energy production in cancer cells, without significantly interfering with the energy production mechanism of surrounding normal cells. The present method accomplishes this by acting on the protons of the membrane constituting the temporary energy storage mechanism in a cancer cell, specifically by changing the natural or resonant frequency of the proton spin via a magnetic field. Alternatively, implementation of the present method acts upon the electron carrier proteins of the electron transport chain by impinging on the natural or resonant frequency of the carbon or nitrogen nuclei of these proteins. Since the velocity of movement of the protein in the cancer cell is higher than in the normal cell, decreasing this velocity will decrease energy production.

The present EMR treatment acts directly on the carbon and nitrogen atoms and protons of the proteins composing the electron transfer system of cancer cells. This is accomplished by altering their spin frequency, which decreases the efficiency of electron transport. Further, selection of the frequency, intensity, and direction of an amount of Electromagnetic radiation applied to cancer cells, referred to as target cells herein, in accordance with the present EMR treatment regimen alters the energy level and movement of the protons to decrease ATP production of the cancer cell, without significantly affecting the normal cells. Accordingly, the rate of production of ATP by the cancer cell is diminished, while the rate of production of ATP by the normal cell, which is normally less than that of the cancer cell, remains substantially unaffected. Moreover, the electrical charges associated with ATP and the resulting ADP, AMP, and pyrophosphate, which evolved as energy rich phosphate bonds, can be broken via implementation of the present EMR treatment regimen to reduce the amount of ATP available to the cancer cell.

In at least embodiment, implementation of the EMR treatment regimen in accordance with the present disclosure significantly diminishes ATP production by affecting the mitochondrial membrane protons. EMR treatment in accordance with the present disclosure acts directly on the protons and electron transport proteins to diminish ATP production, instead of blocking it, so as not to significantly affect normal cells.

An increased effect on the electron transport chain proteins is realized via utilization of radio frequency ("RF") electromagnetic radiation, as discussed in further detail below. An increase in the spin frequency of protons denotes an increase in energy, and a decrease in the spin frequency represents a decrease in energy. An increase in spin frequency is accomplished by an application of RF electromagnetic radiation at a frequency greater than the resting spin frequency. Similarly, a decrease in spin frequency is accomplished by the application of RF electromagnetic radiation having a frequency less than the resting spin frequency. An increase in spin frequency adds energy to power the electron transport system, while a decrease in spin frequency slows the electron transport system.

Additionally, implementation of the present EMR treatment regimen alters the excitation times of protons within cancer cells in a specific tissue, such as cancer. Specifically, as the present EMR treatment interferes with the control system of cancer cells, particularly through the application of RF electromagnetic radiation, the cancer cells are reprogrammed to a more normal cell profile. As this occurs, the protons of the target cells adopt excitation times closer to those of protons in normal cells. Further, the present EMR treatment affects the energy molecules ATP, ADP or AMP to prevent electron transfer from each molecule's orbital by causing the electron to fall to a lower energy orbital, thus reducing the energy available to the cell overall.

Upon implementation of the EMR treatment regimen, the electron transport chain system of the target cell releases the energy it has absorbed from the EMR field at the end of the transport path, according to the following formula:

$$dE/dx \alpha Z^2 \rho/v^2$$

where dE is the energy released, dx is the length of the pathway, v is the velocity of the transport system, Z is the charge (proton and electron) deposited at the molecular end site, and $\rho$ is the charge density at the molecular end site. An approximate value for the electron energy, as an example, is 10 Kilo electron volts ("Kev"), and 17 Kev for the proton.

The present EMR treatment also acts on protons of proteins and DNA, however, it does not breakup the protein or DNA molecule, rather, the present treatment minimizes carrying out of their respective functions.

Cytochrome C

Another way implementation of the present EMR treatment regimen acts to significantly reduce the energy available to a cancer cell, without significantly interfering with surrounding normal cells, is by interfering with the energy mechanism via magnetic interaction with the heme group of the mitochondrial membrane protein cytochrome C. The heme group of cytochrome C comprises iron and, therefore, is capable of magnetic manipulation via EMR treatment in accordance with the present disclosure. Implementation of the present EMR treatment regimen results in magnetization of the iron of the heme group of cytochrome C, which displaces or dislodges cytochrome C from the inner mitochondrial membrane, thus interfering with the electron transport chain and ATP synthesis, and ultimately, resulting in apoptosis, or cell death.

Specifically, cytochrome C is loosely held or associated with the inner mitochondrial membrane by covalent bonds. EMR treatment in accordance with the present disclosure provides a torque on the heme group of cytochrome C by application of a steady magnetic field, and application of low frequency ("LF") electromagnetic radiation vibrates the cytochrome C until it is dislodged and ejected from the membrane. Once cytochrome C is dislodged from the membrane, the electron transport chain is interrupted and ATP synthesis halts. Accordingly, ejection of cytochrome C from the membrane causes apoptosis and eventual death of the cancer cell. However, disruption of cytochrome C can be accomplished without damage to the normal cells by adjusting the level of low frequency (LF) electromagnetic radiation to selectively act only on the increased activity of the cancer cell's inner mitochondrial membrane. Indeed, a magnetic field of sufficient magnitude could be sufficient for EMR treatment to be successful.

Hydrogen Bonds/DNA

The present EMR treatment also acts directly on DNA molecules to prevent the propagation of cancer cells. As in the case of proteins, EMR treatment in accordance with the present disclosure does not break up the DNA molecule, but minimizes its ability to function. For instance, electromagnetic radiation can act on the hydrogen bonds holding together base pairs of DNA. As the hydrogen bonds absorb energy from the electromagnetic radiation, they become excited, and the excitation of the hydrogen bonds can cause the bonds to break. Once some of the hydrogen bonds holding together the strands of DNA are broken, the cancer cells will not be able to replicate, and will eventually die.

In at least one embodiment, implementation of the present EMR treatment regimen alters the charge distribution along a DNA molecule. By altering the charge distribution on a strand of DNA, the function and/or activity of the DNA is modified or nullified. For instance, canceling out a positive charge at a particular location on a DNA molecule can change the three dimensional conformation of the DNA to an inactive form. In another example, EMR treatment in accordance with the present disclosure greatly reduces the attraction between two poles, thereby changing the shape of the molecule from a circular form to a linear form.

It is also possible to change an inactive protein or DNA molecule into an active form with via EMR treatment in accordance with the present disclosure. For example, adding a positive charge to a neutral pole of an inactive protein causes it to assume a circular form in which it is functional. In another example, if the protein is inactive in the linear form and has negative charges at its poles, it can be made active by changing one negative pole to have a positive charge, thereby causing the protein to assume a circular, active form.

Microtubules

The EMR treatment also affects cellular activity of cancer cells through action on a cell's microtubules. A change in the membrane potential is signaled to the nucleus, and vice versa, via microtubules that connect the cellular membrane and nuclear membrane. EMR treatment in accordance with the present disclosure reduces the formation, growth, and dipole magnitude of the microtubules. Since microtubules also play an important role in mitosis and cell growth, implementation of the present EMR treatment regimen also prevents mitosis, or delays mitosis, by preventing or delaying microtubule growth. Further, the present EMR treatment interferes with and delays movement of motor proteins along microtubules.

Illustrative Electromagnetic Radiation Treatment Regimens

The foregoing presented the details of the mechanics and affects of implementation of an electromagnetic radiation ("EMR") treatment regimen in accordance with the present disclosure. As such, and with that understanding, illustrative examples of various specific EMR treatment regimens are presented below with reference to the figures presented herewith.

Electromagnetic Radiation Treatment Regimen

Looking first to FIG. 1, a schematic illustration of an EMR treatment regimen in accordance with the present disclosure is presented and is generally indicated as at 100. To begin, the EMR treatment regimen 100 requires identifying 110 a target area on a patient for treatment. This may be based upon visual observation, such as the presence of a tumor, lesion, or other externally visible indication of the presence of cancer cells. Alternatively, identifying 110 the target area may require non-invasive techniques such as optical or sonic imaging, or invasive techniques, such as, testing of actual tissues samples, in order to detect the presence of cancer cells and define a target area. In at least one embodiment, the target area may be identified to include the patient's entire body.

Once the target area has been identified, the EMR treatment regimen 100 includes isolating 112 the target area for exposure to electromagnetic radiation. Isolating 112 the target area may simply comprise positioning of one or more electromagnetic coils in proximity to the target area. In at least one embodiment, isolating 112 the target area comprises the placement of physical barriers between an electromagnetic radiation source and non-targeted areas of the patient. As one example, a shield, such as a lead shield commonly employed to isolate expose to x-rays, may be positioned over non-targeted areas of the patient's body. Of course, in the event the target area is identified to comprise the patient's entire body, the step of isolated 112 the target area is not required or performed.

The EMR treatment regimen 100 as illustrated in FIG. 1 further comprises selecting 113 a source of electromagnetic radiation. In at least one embodiment, and as presented in the illustrative embodiment of FIG. 2, a low frequency ("LF") electromagnetic radiation source is provided, whereas in the embodiment illustrated in FIG. 3, a radio frequency ("RF") electromagnetic radiation source is provided. In the further illustrative embodiments of FIGS. 4 and 5, both LF and RF electromagnetic radiation sources are provided.

The present EMR treatment regimen 100 further comprises selecting 120 one or more treatment parameters which serve to control the amount of electromagnetic radiation to be applied to the target area of the patient. As previously discussed, the parameters which affect the amount of electromagnetic radiation include the pulse frequency of electromagnetic radiation, the pulse duration of electromagnetic radiation, the amount of electrical current induced by the electromagnetic radiation, the magnetic flux density, and the treatment session exposure time. Each of these parameters is discussed in further detail below with respect to the various types of electromagnetic radiation which may be applied.

Following the selection of one or more EMR treatment parameters, the present EMR treatment regimen 100 further comprises initiating 121 an EMR treatment session. More in particular, each EMR treatment session includes applying 122 an amount of EMR to the target area. Of course, it will be appreciated that the amount of EMR actually applied to the target area is a function of the pulse frequency, the pulse duration, and the treatment session exposure time, as noted above. Once the desired amount of EMR has been applied to the target area, the present EMR treatment regimen 100 includes terminating 123 the EMR treatment session.

In order to determine the effectiveness of the EMR treatment session, the EMR treatment regimen 100 of the illustrative embodiment of FIG. 1 further comprises measuring 124 a response of at least some of the target area cells to the EMR treatment session. As noted above, the excitation duration of protons is appreciably greater when the proton is located in or within the immediate environment of a cancer cell. Thus, a cell's return to a normal state following EMR treatment can be observed by the cancer cell's excitation time becoming essentially the same as the excitation time of a normal cell. Accordingly, the excitation time may be utilized to measure the progress of the EMR treatment regimen 100. In at least one embodiment, the electromagnetic radiation fields generated by the proton are detected via receiver coils. In one further embodiment, a receiver and a demodulator are collectively employed to measure the excitation durations of nuclei in the cancerous tissue via receiver windings. Thus, almost simultaneously with application of the EMR treatment regimen 100, measuring 124 the real time effect of the treatment is possible.

The EMR treatment regimen 100 of the embodiment of FIG. 1 further includes evaluating 125 the response of at least some of the target area cells to the EMR treatment sessions. This evaluation is conducted via a comparison of the measured properties of the target area cells prior to applying 122 the amount of EMR to the target area with the measured properties of the target area cells after applying 122 the amount of EMR thereto. The properties of the target area cells may be measured by a variety of techniques, including MRI and/or blood analysis. For example, blood analysis may be performed to detect the presence of any of a number of serum tumor markers including, but not limited to: carcinoembryonic antigens; CA 125; elevated serum acid phosphatase; human chorionic gonadotropin; $\alpha$-fetoprotein; $\beta_2$-microglobulin; and lactic dehydrogenase.

Low Frequency Electromagnetic Radiation Treatment Regimen

Figure 2:
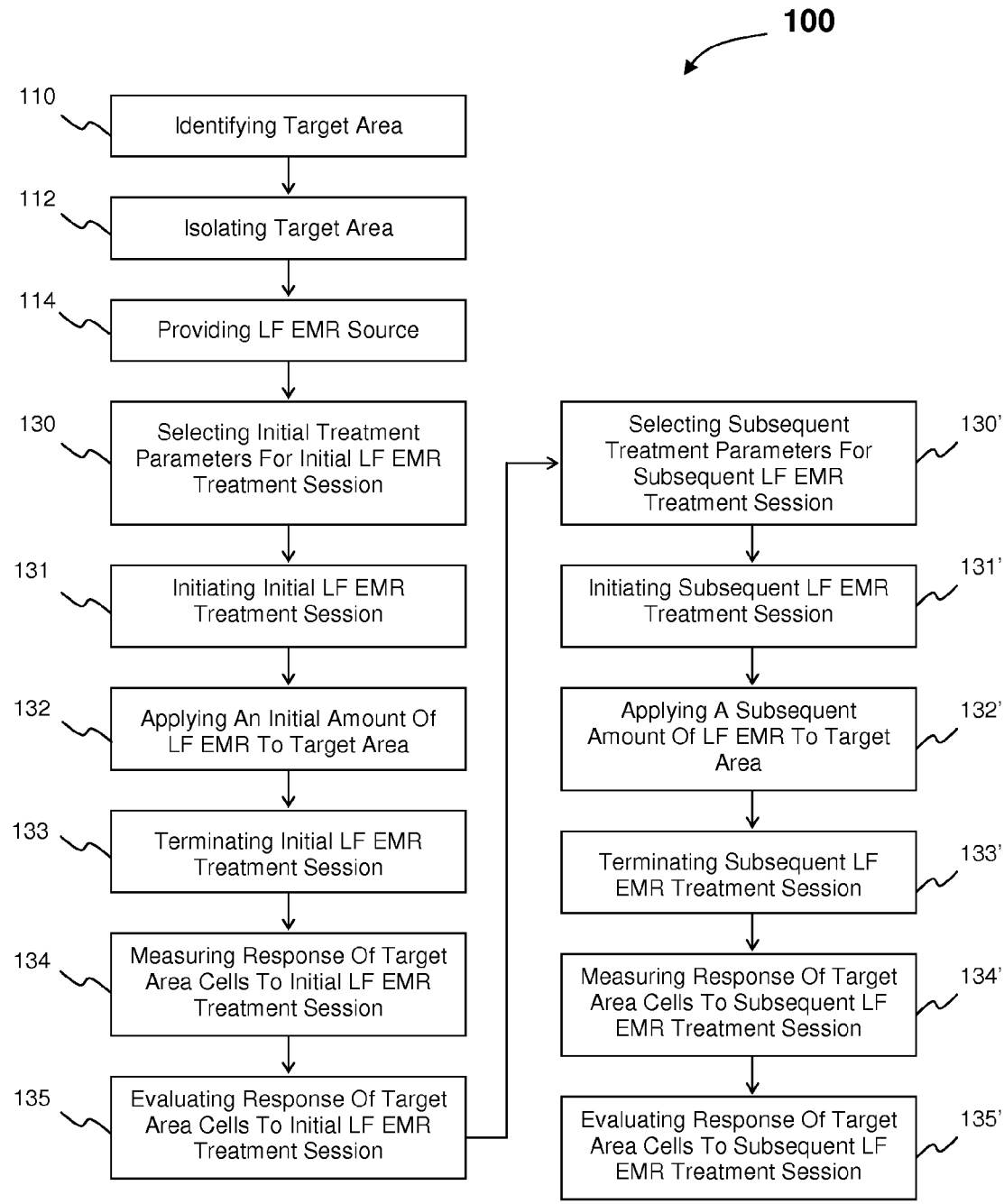
FIG. 2 is a schematic representation illustrative of one embodiment of a low frequency (LF) electromagnetic radiation treatment regimen in accordance with the present disclosure.

FIG. 2 is illustrative of one embodiment of an EMR treatment regimen 100 in accordance with the present disclosure utilizing a low frequency electromagnetic radiation source. As before, the EMR treatment regimen 100 requires identifying 110 a target area on a patient for treatment. Once again, upon identifying 110 the target area, the EMR treatment regimen 100 includes isolating 120 the target area for exposure to electromagnetic radiation. The EMR treatment regimen 100 as illustrated in FIG. 2 further comprises providing 114 a low frequency electromagnetic radiation source.

The embodiment of the EMR treatment regimen 100 illustrated in FIG. 2 further comprises selecting 130 one or more initial treatment parameters which effectively control the amount of low frequency electromagnetic radiation to be initially applied to the target area of the patient. As previously discussed, the treatment parameters which affect the amount of electromagnetic radiation include the pulse frequency, the pulse duration, the amount of electrical current induced by the electromagnetic radiation, the magnetic flux density, and the treatment session exposure time.

In at least one embodiment of the present EMR treatment regimen 100, the treatment parameters selected include one or more of the following. In at least one embodiment, a pulse frequency of the low frequency electromagnetic radiation source is selected to be in a range of about 0.5 hertz to 1000 hertz, and in at least one further embodiment, the pulse frequency is selected in a range of about 0.5 hertz to 200 hertz. A pulse duration in a range of less than or equal to about 300 milliseconds is selected in at least one embodiment of the present EMR treatment regimen. Further, an electrical current in a range of about 0.1 milliampere to 1 ampere may be selected. In addition, in accordance with at least one embodiment of the present disclosure, a magnetic flux density in the range of about 0.5 tesla to 10 tesla may comprise one of the selected treatment parameters. At least one embodiment of the present EMR treatment regimen also includes selecting a treatment exposure time to be in a range from a minimum treatment exposure time of about five (5) seconds to a maximum treatment exposure time of about thirty (30) minutes. Of course, it is understood to be within the scope and intent of the present disclosure for additional treatment parameters to be selected and/or to select one or more of the treatment parameters identified above in an operating range which is different than the operating ranges identified for the illustrative examples presented herein.

Following the selection of one or more initial low frequency EMR treatment parameters, the embodiment of the EMR treatment regimen 100 in accordance with FIG. 2 further comprises initiating 131 an initial low frequency EMR treatment session. More in particular, the initial low frequency EMR treatment session includes applying 132 an initial amount of low frequency EMR to the target area. Of course, it will be appreciated that the amount of EMR actually applied to the target area is a function of the pulse frequency, the pulse duration, and the treatment session exposure time, as noted above. Once the desired amount of EMR has been applied to the target area, the present EMR treatment regimen 100 includes terminating 133 the EMR treatment session.

As before, in order to determine the effectiveness of the initial low frequency EMR treatment session, and in order to allow for adjustment of one or more treatment parameters as may be warranted in order to maximize the effectiveness of the present EMR treatment regimen 100, the illustrative embodiment of the EMR treatment regimen 100 of FIG. 2 further comprises measuring 134 a response of at least some of the target area cells to the initial low frequency EMR treatment session. Measuring 134 the response of the target area cells is performed in the manner discussed above with respect to FIG. 1. Similarly, the EMR treatment regimen 100 of the embodiment of FIG. 2 further includes evaluating 135 the response of at least some of the target area cells to the initial low frequency EMR treatment session in the manner discussed above with respect to FIG. 1.

The illustrative embodiment of the low frequency EMR treatment regimen 100 of FIG. 2 further comprises the steps of: selecting 130' subsequent treatment parameters for one or more subsequent low frequency EMR treatment session(s); initiating 131' a subsequent low frequency EMR treatment session; applying 132' a subsequent amount of low frequency EMR to the target area; terminating 133' the subsequent low frequency EMR treatment session; measuring 134' the response of at least some of the target area cells to the subsequent low frequency EMR treatment session; and, evaluating 135' the response of at least some of the target area cells to the subsequent low frequency treatment session. It will be appreciated that each of the aforementioned subsequent steps is conducted in a manner that equates to the corresponding initial steps 131-135 discussed above, with the exception of selecting 130' the subsequent treatment parameters, which will be informed by the initial measuring 134 and evaluating 135 steps, or by the immediately preceding subsequent measuring 134' and evaluating 135' steps.

Radio Frequency Electromagnetic Radiation Treatment Regimen

Figure 3:
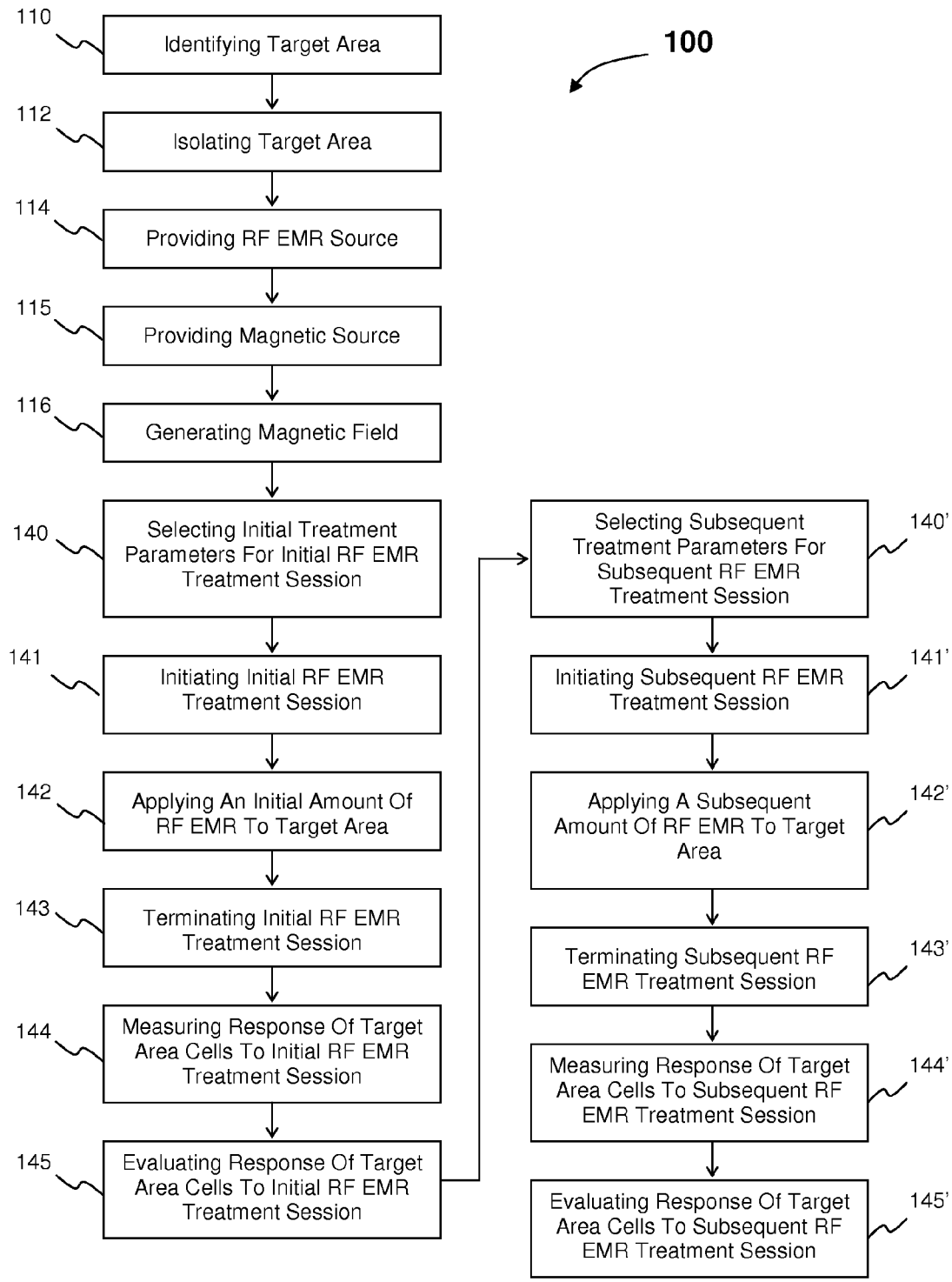
FIG. 3 is a schematic representation illustrative of one embodiment of a radio frequency (RF) electromagnetic radiation treatment regimen in accordance with the present disclosure.

One embodiment of an EMR treatment regimen 100 utilizing a radio frequency electromagnetic radiation source in accordance with the present disclosure is depicted in FIG. 3. As with the previously disclosed embodiments, the EMR treatment regimen 100 of FIG. 3 includes identifying 110 a target area on a patient for treatment. Once again, upon identifying 110 the target area, the EMR treatment regimen 100 includes isolating 112 the target area for exposure to electromagnetic radiation. The EMR treatment regimen 100 as illustrated in FIG. 3 further comprises providing 114 a radio frequency electromagnetic radiation source.

As disclosed above, when utilizing a radio frequency electromagnetic radiation source, a magnetic source is also provided, such as is indicated in FIG. 3 at 115, in proximity to the target area cells. In one embodiment, a magnetic or paramagnetic material is placed in or near the target area by injection of the material into nearby blood vessels. In another embodiment, the magnetic or paramagnetic material is placed externally to the target region, such as with an external magnetic device. Once in position, the magnetic or paramagnetic material is responsible for generating 116 a magnetic field proximate the target area cells.

Following the generation of the magnetic field, the radio frequency EMR treatment regimen 100 as illustrated in FIG. 3 essentially proceeds in a similar manner as the low frequency EMR treatment regimen 100 as illustrated in FIG. 2. Specifically, the radio frequency EMR treatment regimen 100 of FIG. 3 comprises: selecting 140 initial treatment parameters for an initial radio frequency EMR treatment session; initiating 141 an initial radio frequency EMR treatment session; applying 142 an initial amount of radio frequency EMR to the target area; terminating 143 the initial radio frequency EMR treatment session; measuring 144 the response of at least some of the target area cells to the initial radio frequency EMR treatment session; and, evaluating 145 the response of at least some of the target area cells to the initial radio frequency treatment session.

FIG. 3 is also illustrative of the further steps of: selecting 140' subsequent treatment parameters for one or more subsequent radio frequency EMR treatment session(s); initiating 141' a subsequent radio frequency EMR treatment session; applying 142' a subsequent amount of radio frequency EMR to the target area; terminating 143' the subsequent radio frequency EMR treatment session; measuring 134' the response of at least some of the target area cells to the subsequent radio frequency EMR treatment session; and, evaluating 135' the response of at least some of the target area cells to the radio frequency treatment session.

Similar to the low frequency EMR treatment regimen 100, the step of selecting 140' the subsequent treatment parameters, which will be informed by the initial measuring 144 and evaluating 145 steps, or by the immediately preceding subsequent measuring 144' and evaluating 145' steps.

Combined LF/RF Electromagnetic Radiation Treatment Regimen

Figure 4:
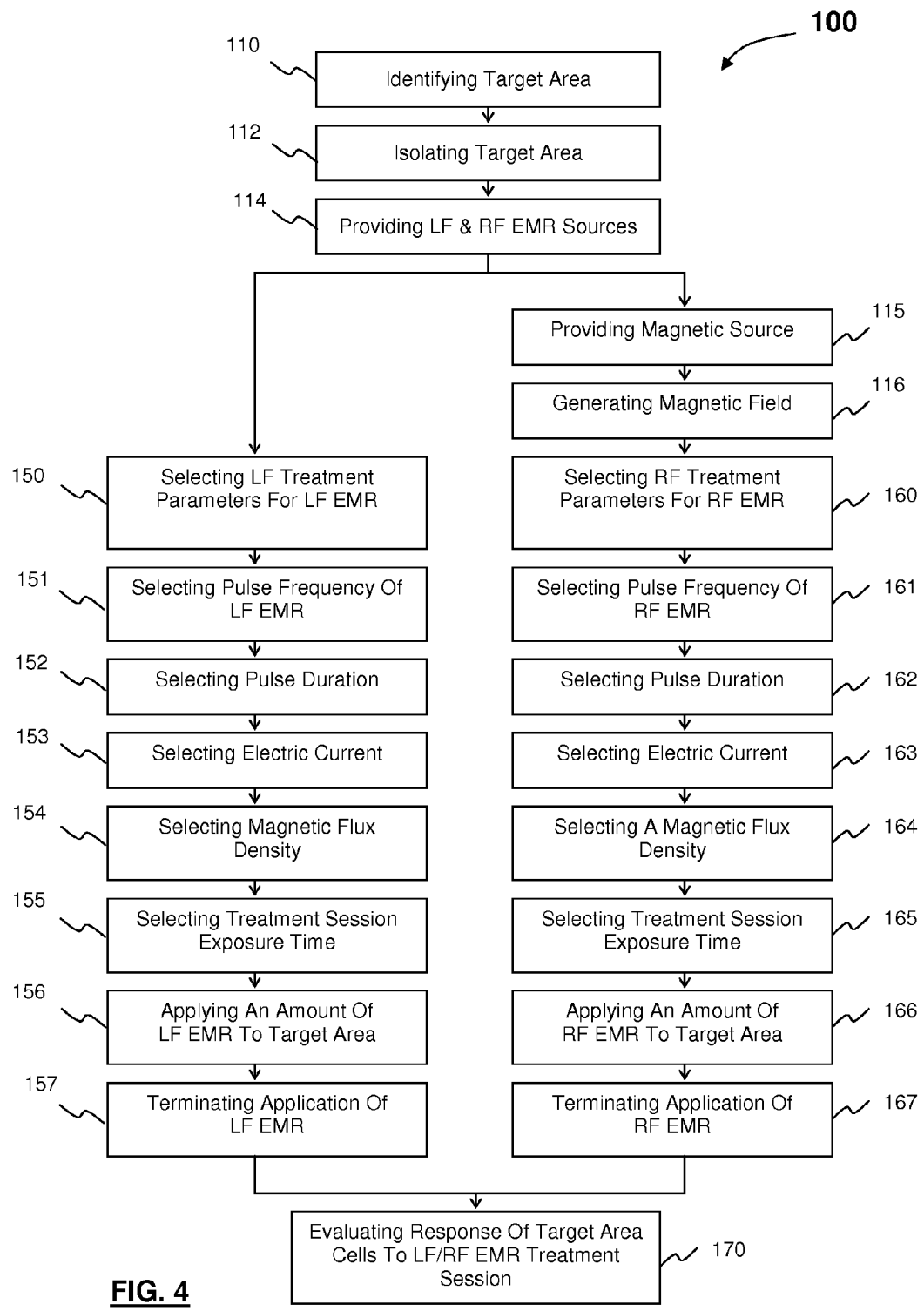
FIG. 4 is a schematic representation illustrative of one embodiment of a combined parallel low frequency (LF) and radio frequency (RF) electromagnetic radiation treatment regimen in accordance with the present disclosure.
Figure 5:
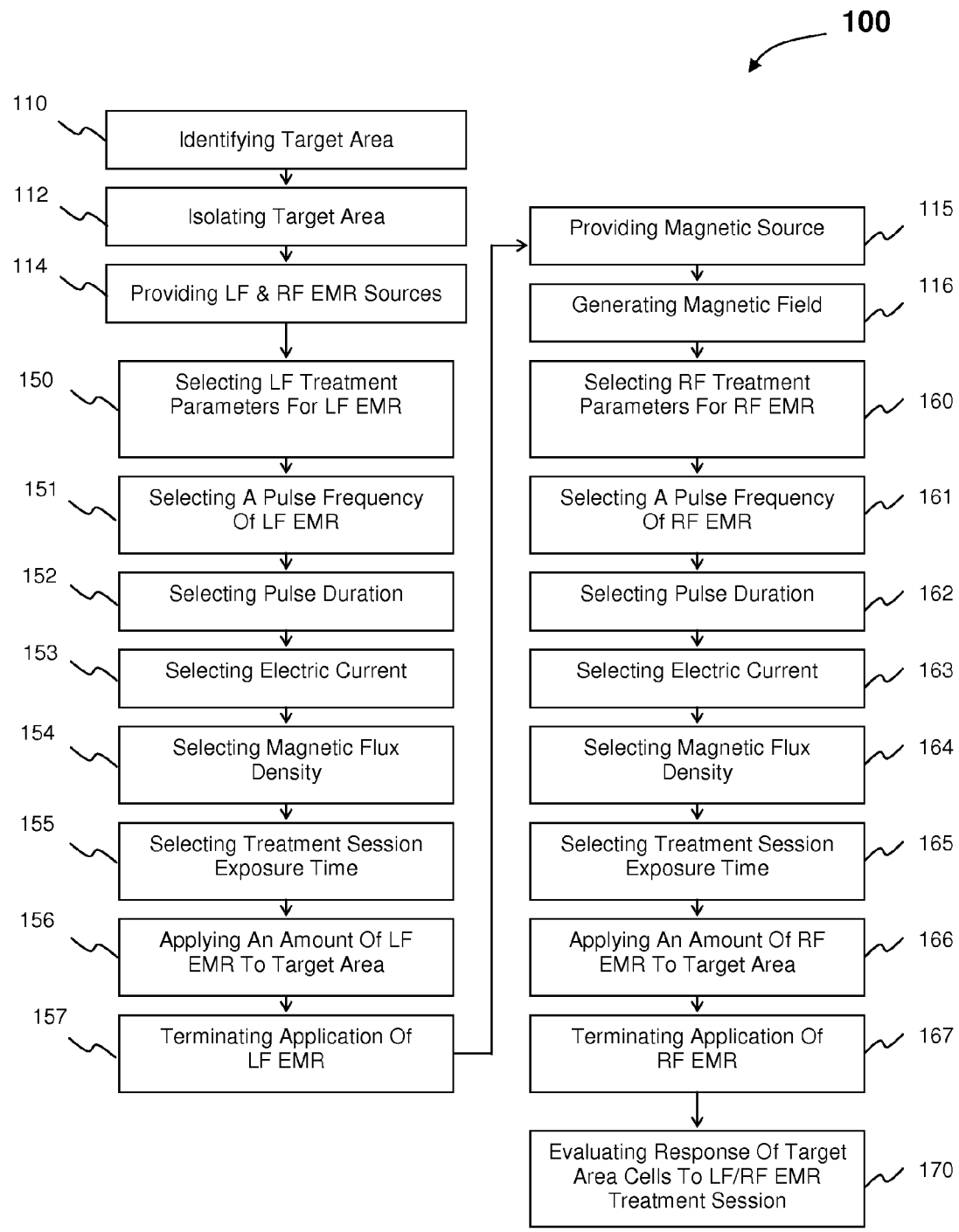
FIG. 5 is a schematic representation illustrative of one embodiment of a combined series low frequency (LF) and radio frequency (RF) electromagnetic radiation treatment regimen in accordance with the present disclosure.

FIGS. 4 and 5 are illustrative of embodiments of EMR treatment regimens 100 in accordance with the present disclosure in which both low frequency and radio frequency electromagnetic radiation are utilized. More in particular, FIG. 4 presents an EMR treatment regimen 100 wherein low frequency electromagnetic radiation is applied to the target area of the patient in parallel with the application of radio frequency electromagnetic radiation, essentially simultaneously. In the alternative embodiment of FIG. 5, the EMR treatment regimen 100 comprises the application of low frequency electromagnetic radiation followed by radio frequency electromagnetic radiation to the target area of the patient, in a series arrangement. Of course, it is within the scope and intent of the present disclosure for an EMR treatment regimen 100 to comprise radio frequency electromagnetic radiation followed by low frequency electromagnetic radiation, as well as series/parallel applications of the same. Further, in a series arrangement, the application of low (or radio) frequency electromagnetic radiation may be immediately followed by radio (or low) frequency electromagnetic radiation, or there may be a rest period between applications, wherein the rest period may be minutes, hors, or even days.

Looking to FIG. 4, the combined EMR treatment regimen comprises the steps of identifying 110 a target area, isolating a target area 112, providing 114 an electromagnetic radiation source, providing a magnetic source 115, and generating 116 a magnetic field, which are each performed in a manner similar to that described above with regard to the embodiments disclosed in FIGS. 1 through 3.

Next, FIGS. 4 and 5 illustrate the EMR treatment regimens 100 comprise selecting 150, 160 treatment parameters for low frequency EMR treatment sessions and radio frequency EMR treatment sessions, respectively. As further illustrated in FIGS. 4 and 5, the step of selecting 150, 160 treatment parameters includes selecting 151, 161 a pulse frequency, selecting 52, 162 pulse duration, selecting 153, 163 an electrical current, selecting 154, 164 a magnetic flux density, and selecting 155, 165 an exposure time.

Once the treatment parameters have been selected, the EMR treatment regimens 100 of FIGS. 4 and 5 include applying 156, 166 and amount of low frequency EMR and radio frequency EMR, respectively. The step of applying 156, 166 the low and radio frequency EMR occurs essentially simultaneously in the parallel configuration of FIG. 4, and one after the other in the series configuration in the illustrative embodiment of FIG. 5. The EMR treatment regimens 100 of the embodiments of FIGS. 4 and 5 further comprise terminating 157, 167 the application of low and radio frequency EMR, respectively.

As in the preceding embodiments, the EMR treatment regimens 100 of the illustrative embodiments of FIGS. 4 and 5 further comprise evaluation 170 the response of at least some of the target area cells to the low frequency EMR and radio frequency EMR treatment sessions.

Figure 6:
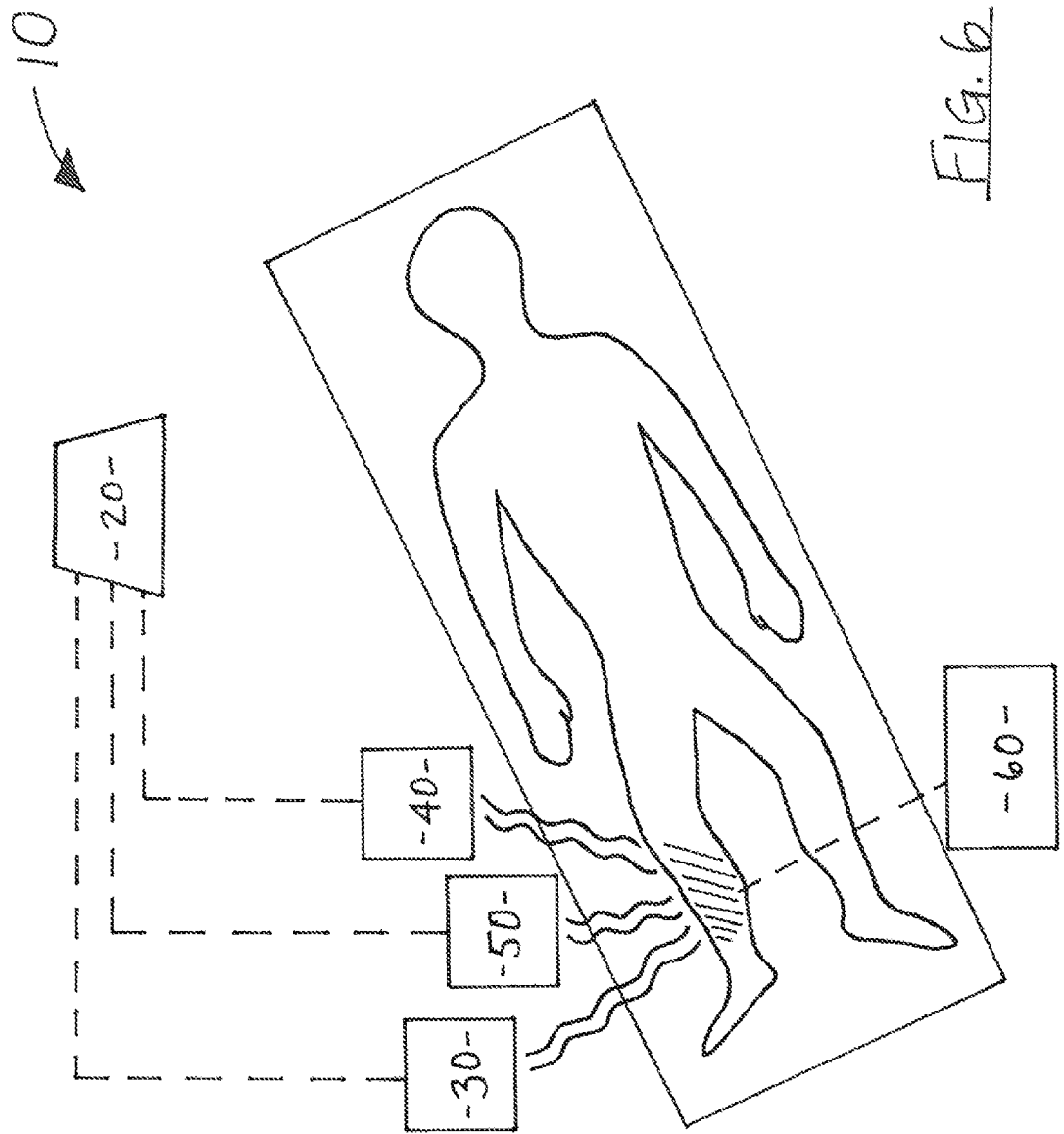
FIG. 6 is a schematic representation illustrative of one embodiment of a system for conducting an electromagnetic radiation treatment session in accordance with the present disclosure.

FIG. 6 is a schematic representation of system 10 for conducting an EMR treatment regimen in accordance with the present disclosure. More in particular, the system 10 comprises a controller 20, which is utilized for the selection of the treatment parameters for any particular treatment sessions. Further, the system 10 includes a source of low frequency electromagnetic radiation 30 and a source of radio frequency electromagnetic radiation 40. A magnetic source 50 is included for utilization in a radio frequency EMR treatment session.

FIG. 6 further illustrates that the source of low frequency EMR 30, radio frequency EMR 40, and the magnetic source 50 are each disposed proximate at least a portion of the patient, i.e., the target area. Additionally, the system 10 comprises at least one detector 60, which is also disposed proximate the patient, the detector 60 being operative to measure a response of at least some of the cells in the target area to EMR treatment, for evaluation by treating physician/technician.

Early Detection of Cancer

The detection of cancer can come relatively late in its development. The present EMR treatment regimen offers two solutions to this problem. First, the safety profile of the EMR treatment permits its use without a definitive diagnosis. Second, detection of the excitation signals of cancer cells allow an earlier diagnosis via implementation of the EMR treatment regimen of the present disclosure than with previously known methods.

The detection of cancer is very difficult before one gram of tumor cells is present, which represents about one billion cells, and 30 doublings in volume. Ten further doublings in volume would represent about one kilogram of these tumor cells, which could be lethal. Thus cancer cells may be able to metastasize prior to detection. This also means that tumor study occurs over a late, relatively short period of total growth. Because of its safety profile, the present EMR treatment regimen may be utilized when cancer is possible, but not certain, to detect and treat the cancer cells.

Portable Adjunct Treatment Device

A supplementary treatment may be implemented between EMR treatments via an implanted electrical device. Such an adjunct treatment device may consist of a microcomputer controlled electrical generator implanted beneath the skin in the region of a cancerous tissue or organ. Electrical connections are positioned between the generator to an electrode placed approximately in the center of the cancerous tissue, and another electrode placed beyond the limit, or on the periphery of the cancer cells. The electrodes may be placed in or near the cancer cells or cancerous tissue, or on the skin adjacent to this tissue. In at least one embodiment, the electrodes are placed to maximize the current reaching the cancer cells. The polarity of the electrodes would be either positive or negative, determining the direction of the electric field or the current. A positive polarity of an electrode disposed in the interior of cancerous tissue would lead to a decrease in malignancy.

This adjunct treatment device may comprise a small battery powered generator with microcomputer, which can be attached by various means to parts of the body or clothing, and worn comfortably by the patient throughout the day or evening involving usual activities or sleep. Alternatively, the device can be implanted in or near cancerous tissue. Such a device is intended as an adjunct to EMR treatment in accordance with the present disclosure, and can be activated for periods of time between EMR treatments. The current, frequency, and other parameters are adjusted to meet the needs of the patient and type of character of the cancer cell, primarily to depolarize or hyperpolarize the membrane potentials. In one embodiment, the positive pole is placed in the approximate center of the mass of cancerous tissue, and the negative pole peripherally or externally thereto.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method of treating cancer cells with electromagnetic radiation comprising the steps of:

identifying a target area for treatment comprising a plurality of target area cells, wherein at least some of the target area cells comprise cancer cells, isolating the target area from surrounding areas, providing at least one magnetic source, applying a magnetic field affecting at least some of the plurality of target area cells, selecting low frequency treatment parameters for a low frequency electromagnetic radiation treatment session, selecting radio frequency treatment parameters for a radio frequency electromagnetic radiation treatment session, applying an amount of low frequency electromagnetic radiation from a low frequency electromagnetic radiation source to the target area in accordance with the low frequency treatment parameters, applying an amount of radio frequency electromagnetic radiation from a radio frequency electromagnetic radiation source to the target area in accordance with the radio frequency treatment parameters, terminating the application of the low frequency electromagnetic radiation to the target area, terminating the application of the radio frequency electromagnetic radiation to the target area, and measuring a response of at least some of the cancer cells in the target area to the low frequency electromagnetic radiation treatment session and the radio frequency electromagnetic radiation treatment session.

2. The method as recited in claim 1 further comprising separately applying the amount of low frequency electromagnetic radiation to the target area and applying the amount of radio frequency electromagnetic radiation to the target area in a series treatment regimen.

3. The method as recited in claim 1 further comprising concurrently applying the amount of low frequency electromagnetic radiation to the target area and applying the amount of radio frequency electromagnetic radiation to the target area in a parallel treatment regimen.

4. The method as recited in claim 1 wherein the low frequency electromagnetic radiation treatment session reduces a microtubule growth rate in at least some of the cancer cells in the target area.

5. The method as recited in claim 1 wherein the radio frequency electromagnetic radiation treatment session initiates apoptosis in at least some of the cancer cells in the target area.

6. The method as recited in claim 1 wherein the radio frequency electromagnetic radiation treatment session reduces ATP production in at least some of the cancer cells in the target area.

7. The method as recited in claim 1 wherein each of the low frequency treatment parameters and the radio frequency treatment parameters comprise at least one of a pulse duration, an electrical current, a magnetic flux density, or a treatment session exposure time.

8. The method as recited in claim 7 wherein the low frequency treatment parameters further comprise selecting a pulse frequency in a range of about 0.5 hertz to 1000 hertz.

9. The method as recited in claim 7 further comprising selecting the pulse duration in a range of less than or equal to about 300 milliseconds.

10. The method as recited in claim 7 further comprising selecting the electrical current in a range of about 0.1 milliampere to 1 ampere.

11. The method as recited in claim 7 further comprising selecting the magnetic flux density in the range of about 0.5 tesla to 10 tesla.

12. The method as recited in claim 7 further comprising selecting the treatment exposure time to be in a range from about five seconds to about thirty minutes.

13. A method of treating cancer cells with electromagnetic radiation comprising the steps of:

identifying a target area for treatment comprising a plurality of target area cells, wherein at least some of the target area cells comprise cancer cells, isolating the target area from surrounding areas, providing at least one magnetic source, generating a magnetic field affecting at least some of the plurality of target area cells, selecting initial low frequency treatment parameters for an initial low frequency electromagnetic radiation treatment session, selecting initial radio frequency treatment parameters for an initial radio frequency electromagnetic radiation treatment session, applying an initial amount of low frequency electromagnetic radiation from a low frequency electromagnetic radiation source to the target area in accordance with the initial low frequency treatment parameters, applying an initial amount of radio frequency electromagnetic radiation from a radio frequency electromagnetic radiation source to the target area in accordance with the initial radio frequency treatment parameters, terminating the application of the low frequency electromagnetic radiation to the target area, terminating the application of the radio frequency electromagnetic radiation to the target area, measuring a response of at least some of the cancer cells in the target area to the initial low frequency electromagnetic radiation treatment session and the initial radio frequency electromagnetic radiation treatment session, evaluating the measured response of the cancer cells in the target area to the initial low frequency electromagnetic radiation treatment session and the initial radio frequency electromagnetic radiation treatment session, selecting subsequent low frequency treatment parameters for a subsequent low frequency electromagnetic radiation treatment session, selecting subsequent radio frequency treatment parameters for a subsequent radio frequency electromagnetic radiation treatment session, initiating the subsequent low frequency electromagnetic radiation treatment session, initiating the subsequent radio frequency electromagnetic radiation treatment session, applying a subsequent amount of low frequency electromagnetic radiation from the low frequency electromagnetic radiation source to the target area in accordance with the subsequent low frequency treatment parameters, applying a subsequent amount of radio frequency electromagnetic radiation from the radio frequency electromagnetic radiation source to the target area in accordance with the subsequent radio frequency treatment parameters, terminating the subsequent low frequency electromagnetic radiation treatment session, terminating the subsequent radio frequency electromagnetic radiation treatment session, measuring a response of at least some of the cancer cells in the target area to the subsequent low frequency electromagnetic radiation treatment session and the subsequent radio frequency electromagnetic radiation treatment session, and evaluating the measured response of the cancer cells in the target area to the subsequent low frequency electromagnetic radiation treatment session and the subsequent radio frequency electromagnetic radiation treatment session.

14. The method as recited in claim 13 wherein measuring the response of at least some of the cancer cells in the target area comprises capturing at least one image of the target area by magnetic resonance imaging.

15. The method as recited in claim 13 wherein the response of at least some of the cancer cells in the target area is a change in a cell growth rate.

16. The method as recited in claim 13 wherein the low frequency electromagnetic radiation source comprises at least one electromagnetic coil.

17. The method as recited in claim 13 wherein the magnetic field comprises a steady state magnetic field.

18. The method as recited in claim 13 wherein the magnetic field comprises a pulsed magnetic field.

19. The method as recited in claim 13 further comprising doping the target area with an amount of a magnetic substance to enhance the efficiency of the radio frequency electromagnetic radiation treatment session, wherein the magnetic substance is independent of the at least one magnetic source.

* * * * *